United States Patent
Cartman et al.

(10) Patent No.: US 11,136,603 B2
(45) Date of Patent: Oct. 5, 2021

(54) MATERIALS AND METHODS FOR DIRECTING CARBON FLUX AND INCREASED PRODUCTION OF 7-AMINOHEPTANOIC ACID OR 6-AMINOHEXANOIC ACID

(71) Applicant: INV Nylon Chemicals Americas, LLC, Wilmington, DE (US)

(72) Inventors: Stephen Cartman, Stockton-on-Tees (GB); Jonathan Combe, North Yorkshire (GB); Alexander B. Foster, Yarm (GB); Jonathan Kennedy, North Yorkshire (GB)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 0 days.

(21) Appl. No.: 15/656,482

(22) Filed: Jul. 21, 2017

(65) Prior Publication Data
US 2018/0023104 A1 Jan. 25, 2018

Related U.S. Application Data

(60) Provisional application No. 62/366,597, filed on Jul. 25, 2016.

(51) Int. Cl.
| | |
|---|---|
| *C12P 13/00* | (2006.01) |
| *C08G 69/08* | (2006.01) |
| *C08G 69/10* | (2006.01) |
| *C12N 9/04* | (2006.01) |
| *C12N 9/02* | (2006.01) |
| *C12N 9/10* | (2006.01) |
| *C12N 15/52* | (2006.01) |

(52) U.S. Cl.
CPC ........... *C12P 13/005* (2013.01); *C08G 69/08* (2013.01); *C08G 69/10* (2013.01); *C12N 9/0006* (2013.01); *C12N 9/0008* (2013.01); *C12N 9/1029* (2013.01); *C12N 9/1096* (2013.01); *C12N 15/52* (2013.01); *C12Y 101/01021* (2013.01); *C12Y 102/01003* (2013.01); *C12Y 102/99006* (2013.01); *C12Y 203/01009* (2013.01); *C12Y 206/01* (2013.01)

(58) Field of Classification Search
None
See application file for complete search history.

(56) References Cited

U.S. PATENT DOCUMENTS

| | | | | |
|---|---|---|---|---|
| 7,695,949 B2* | 4/2010 | Hohmann | ............... | C12P 13/02 435/252.3 |
| 8,097,439 B2* | 1/2012 | Alibhai | ............... | C12N 9/0006 435/147 |
| 10,006,055 B2* | 6/2018 | Burk | ...................... | C12N 15/52 |
| 2014/0186904 A1 | 7/2014 | Botes et al. | | |
| 2014/0193863 A1 | 7/2014 | Botes et al. | .......... | C12P 13/001 |
| 2014/0199737 A1 | 7/2014 | Botes et al. | | |
| 2014/0242655 A1 | 8/2014 | Pearlman et al. | | |
| 2015/0322464 A1 | 11/2015 | Atsumi et al. | ............. | C12P 7/24 |
| 2016/0201097 A1 | 7/2016 | Botes et al. | .......... | C12P 7/6409 |
| 2017/0159082 A1 | 6/2017 | Conradie et al. | .......... | C12P 7/26 |
| 2018/0023102 A1* | 1/2018 | Foster | .................. | C12Y 206/01 435/128 |

OTHER PUBLICATIONS

Rodriguez et al. (Metabolic Engin., vol. 25, 2014, pp. 227-237).*
Papanikolaou et al., "Citric Acid Production by Yarrowia Lipolytica Cultivated on Olive-Mill Wastewater-Based Media", Bioresource Technology, vol. 99, No. 7, 2008, pp. 2419-2428.
Pearson et al., "Improved Tools for Biological Sequence Comparison", Proceedings of the National Academy of Sciences, Biochemistry, vol. 85, Apr. 1988, pp. 2444-2448.
Perez-Pantoja et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, Aug. 7, 2008, pp. 736-794.
Przybylski et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, 2012, 9 pages.
Ramsay et al., "Use of a Nylon Manufacturing Waste as an industrial Fermentation Substrate", Applied and Environmental Microbiology, vol. 52, No. 1, Jul. 1986, pp. 152-156.
Rodriguez et al., "Isobutyraldehyde Production from *Escherichia coli* by Removing Aldehyde Reductase Activity", Microbial Cell Factories, vol. 11, No. 90, 2012, pp. 1-11.
Rodriguez et al., "Toward Aldehyde and Alkane Production by Removing Aldehyde Reductase Activity in *Escherichia coli*", Metabolic Engineering, vol. 25, 2014, 37 pages.
Samsonova et al., "Molecular Cloning and Characterization of *Escherichia coli* K12 ygjG Gene", BMC Microbiology, vol. 3, No. 2, Jan. 31, 2003, pp. 1-10.

(Continued)

*Primary Examiner* — Hope A Robinson

(57) ABSTRACT

This disclosure relates to genome-scale attenuation or knockout strategies for directing carbon flux to certain carbon based building blocks within the 7-aminoheptanoic acid (7-AHA) and 6-aminohexanoic acid (6-AHA) biosynthesis pathways, for example, to achieve reduced flux to unwanted side products while achieving increased production of desired intermediates and end products. This disclosure also relates to non-naturally occurring mutant bacterial strains comprising one or more gene disruptions in aldehyde reductase and/or aldehyde dehydrogenase genes that are generated to direct carbon flux to certain carbon based building blocks. This disclosure further relates to a method for enhancing production of carbon based building blocks by generating non-naturally occurring mutant bacterial strains, culturing said mutant bacterial strains in the presence of suitable substrates or under desired growth conditions, and substantially purifying the desired end product.

5 Claims, 13 Drawing Sheets
Specification includes a Sequence Listing.

(56) References Cited

OTHER PUBLICATIONS

Sanders et al., "Characterization of the Human ω-Oxidation Pathway for ω-Hydroxy-Very-Long-Chain Fatty Acids", The FASEB Journal, Research Communication, vol. 22, No. 6, Jun. 2008, pp. 2064-2071.
Sanders et al., "Evidence for Two Enzymatic Pathways for w-Oxidation of Docosanoic Acid in Rat Liver Microsomes", Journal of Lipid Research, vol. 46, May 2005, pp. 1001-1008.
Seedorf et al., "The Genome of Clostridium Kluyveri, A Strict Anaerobe with Unique Metabolic Features", PNAS USA, vol. 105, No. 6, Feb. 12, 2008, pp. 2128-2133.
Shen et al., "Driving Forces Enable High-Titer Anaerobic 1-Butanol Synthesis in *Escherichia coli*", Applied and Environmental Microbiology, vol. 77, No. 9, May 2011, pp. 2905-2915.
Stanbury et al., "Principles of Fermentation Technology", 2nd edition, Aeration and Agitation, 1995, 14 pages.
Streit et al., "Biotin in Microbes, the Genes Involved in its Biosynthesis, its Biochemical Role and Perspectives for Biotechnological Production", Applied Microbiology and Biotechnology, vol. 61, Issue 1, Mar. 2003, pp. 21-31.
Suzuki et al., "GriC and GriD Constitute a Carboxylic Acid Reductase Involved in Grixazone Biosynthesis in Streptomyces Griseus", Journal of Antibiotics, vol. 60, No. 6, 2007, pp. 380-387.
Trapnell et al., "Differential Gene and Transcript Expression Analysis of RNA-Seq Experiments with TopHat and Cufflinks", Mar. 1, 2012, 39 pages.
Venkitasubramanian et al., "Aldehyde Oxidoreductase as a Biocatalyst: Reductions of Vanillic Acid", Enzyme and Microbial Technology, vol. 42, No. 2, Jan. 2008, pp. 130-137.
Wee et al., "Biotechnological Production of Lactic Acid and Its Recent Applications", Food Technology and Biotechnology, vol. 44, No. 2, 2006, pp. 163-172.
Woolridge et al., "Efflux of the Natural Polyamine Spermidine Facilitated by the Bacillus Subtilis Multidrug Transporter Blt", The Journal of Biological Chemistry, vol. 272, No. 14, Apr. 4, 1997, pp. 8864-8866.
Yang et al., "Value-Added Uses for Crude Glycerol—a Byproduct of Biodiesel Production", Biotechnology for Biofuels, vol. 5, No. 13, 2012, pp. 1-10.
Yonaha et al., "4-Aminobutyrate : 2-Oxoglutarate Aminotransferase of Streptomyces Griseus : Purification and Properties", European Journal of Biochemistry, vol. 146, Jan. 1985, pp. 101-106.
Altschul et al., "Gapped Blast and PSI-Blast: A New Generation of Protein Database Search Programs", Nucleic Acids Research (NCIB NLM NIH), Bethesda Md., NAR, vol. 25, No. 17, Jul. 16, 1997, pp. 3389-3402.
Ausubel et al., "Current Protocols in Molecular Biology", Greene Publishing Associates/Wiley Interscience, New York, Supplement 30, section 7.7.18, 1987, 1 page.
Barker et al., "Enzymatic Reactions in the Degradation of 5-Aminovalerate by Clostridium Aminovalericum", The Journal of Biological Chemistry, vol. 262, No. 19, Jul. 5, 1987, pp. 8994-9003.
Beld et al., "Fatty Acid Biosynthesis Revisited: Structure Elucidation and Metabolic Engineering", Mol. Biosyst., vol. 11, No. 1, Jan. 2, 2015, 44 pages.
Bellmann et al., "Expression Control and Specificity of the Basic Amino Acid Exporter LysE of Corynebacterium Glutamicum", Microbiology, vol. 147, Jul. 1, 2001, pp. 1765-1774.
Bugg et al., "The Emerging Role for Bacteria in Lignin Degradation and Bio-Product Formation", Current Opinion in Biotechnology, vol. 22, 2011, pp. 394-400.
Datsenko et al., "One-Step Inactivation of Chromosomal Genes in *Escherichia coli* K-12 Using PCR Products", PNAS, vol. 97, No. 12, Jun. 6, 2000, pp. 6640-6645.
Demain et al., "Manual of Industrial Microbiology and Biotechnology", 2nd Edition, Scale-Up of Microbial Processes, ASM Press, 1999, 5 pages.
Elkins et al., "Substrate Specificity of the RND-Type Multidrug Efflux Pumps AcrB and AcrD of *Escherichia coli* Is Determined Predominately by Two Large Periplasmic Loops", Journal of Bactiriology, vol. 184, No. 23, Dec. 2002, pp. 6490-6498.
Genbank, "Adenosylmethionine-8-Amino-7-Oxorionanoate Aminotransferase [Rhodobacter Sphaeroides 2.4.1]", Accession No. ABA81135.1, Jul. 20, 2015, 2 pages.
Genbank, "Alcohol Dehydrogenase [Geobaciiius Stearothermophilus]", Accession No. CAA81612.1, Apr. 18, 2005, 2 pages.
Genbank, "Aminotransferase Class-III [Pseudomonas Syringae Pv. Syringae B728a]", Accession No. AAY39893.1, Jan. 31, 2014, 2 pages.
Genbank, "Fatty-Acid-CoA Ligase FadD9 [*Mycobacterium marinurn* M]", Accession No. ACC40567.1, Jan. 31, 2014, 2 pages.
Genbank, "NAD Dependent Epimerase/Dehydratase Family Protein [*Mycobacterium smegrnatis* Str. MC2 155]", Accession No. ABK75684.1, Jan. 31, 2014, 2 pages.
Genbank, "ORF_o387 [*Escherichia coli* Str. K-12 Substr. MG1655]", Accession No. AAA69178.1, Jul. 1, 1995, 1 page.
Genbank, "ORF_o496 [*Escherichia coli* Str. K-12 Substr. MG1655]", Accession No. AAA57874.1, Nov. 21, 2011, 2 pages.
Genbank, "Probable Aminotransferase [Chromobacterium Violaceurn ATCC 12472]", Accession No. AAQ59697.1, Jan. 31, 2014, 2 pages.
Genbank, "Probable Class III Aminotransferase [Pseudomonas Aeruginosa PAO1]", Accession No. AAG08191,1, Jan. 31, 2014, 2 pages.
Genbank, "Putative Fatty-Acid-CoA Ligase FADD9 [*Mycobacterium abscessus* Subsp. Bolletii 2B-0307]", Accession No. EIV11143.1, Dec. 19, 2014, 2 pages.
Genbank, "Putative Long-Chain Fatty-Acid-CoA Ligase [*Mycobacterium smegmatis* Str. MC2 155]", Accession No. ABK71854.1, Jan. 31, 2014, 2 pages.
Genbank, "Pyruvate Transaminase [Vibrio Fluvialis]", Accession No. AEA39183.1, Apr. 4, 2011, 1 page.
Genbank, "Thioester Reductase Domain Protein [Segniliparus Rotundus DSM 44985]", Accession No. ADG98140.1, Jan. 28, 2014, 2 pages.
Genbank, "Thioester Reductase Domain-Containing Protein [Segniliparus Rugosus ATCC BAA-974]", Accession No. EFV11917.1, Sep. 9, 2013, 3 pages.
Genbank, "Unknown [*Saccharomyces cerevisiae*]", Accession No. CAA90636.1, Jul. 14, 2016, 2 pages.
Guerrillot et al., "Purification and Characterization of Two Aldehyde Dehydrogenases from Pseudomonas Aeruginosa", European Journal of Biochemistry, vol. 81, Nov. 1977, pp. 185-192.
Harwood et al., "The Beta-Ketoadipate Pathway and the Biology of Self-Identity", Annual Review of Microbiology, vol. 50, Oct. 1996, pp. 553-590.
Hermann, Thomas, "Industrial Production of Amino Acids by Coryneform Bacteria", Journal of Biotechnology, vol. 104, 2003, pp. 155-172.
Huhn et al., "Identification of the Membrane Protein SucE and its Role in Succinate Transport in Corynebacterium Glutamicum", Applied Microbiology and Biotechnology, vol. 89, Jan. 2011, pp. 327-335.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase", Applied and Environmental Microbiology, vol. 68, No. 11, Nov. 2002, pp. 5671-5684.
Iwaki et al., "Identification of a Transcriptional Activator (ChnR) and a 6-Oxohexanoate Dehydrogenase (ChnE) in the Cyclohexanol Catabolic Pathway in *Acinetobacter* Sp. Strain NCIMB 9871 and Localization of the Genes That Encode Them", Applied and Environmental Microbiology, vol. 65, No. 11, Nov. 1999, pp. 5158-5162.
Jarboe, Laura R., "YghD: A Broad-Substrate Range Aldehyde Reductase with Various Applications in Production of Biorenewable Fuels and Chemicals", Appl. Microbiol. Biotechnol., vol. 89, No. 2, 2011, pp. 249-257.
Jaremko et al., "The Initial Metabolic Conversion of Levulinic Acid in Cupriavidus Necator", Journal of Biotechnology, vol. 155, 2011, pp. 293-298.

(56) References Cited

OTHER PUBLICATIONS

Kaulmann et al., "Substrate Spectrum of ω-Transaminase from Chromobacterium Violaceum DSM30191 and its Potential for Biocatalysts", Enzyme and Microbial Technology, vol. 41, Oct. 2007, pp. 628-637.
Kim, Ki-Han, "Purification and Properties of a Mine α-Ketoglutarate Transaminase from *Escherichia coli*", The Journal of Biological Chemistry, vol. 239, No. 3, Mar. 1, 1964, pp. 783-786.
Kopke et al., "2,3-Butanediol Production by Acetogenic Bacteria, an Alternative Route to Chemical Synthesis, Using Industrial Waste Gas", Applied and Environmental Microbiology, vol. 77, No. 15, Aug. 2011, pp. 5467-5475.
Larroy et al., "Characterization of the *Saccharomyces cerevisiae* YMR318C (ADH6) Gene Product as a Broad Specificity NADPH-Dependent Alcohol Dehydrogenase: Relevance in Aldehyde Reduction", Biochem Journal, vol. 361, No. 1, Jan. 1, 2002, pp. 163-172.
Latham et al., "Divergence of Substrate Specificity and Function in the *Escherichia coli* Hotdog-Fold Thioesterase Paralogs YdiI and YbdB", Biochemistry, vol. 53, No. 29, Jul. 29, 2014, pp. 4775-4787.
Lee et al., "Synthesis of Pure Meso-2,3-Butanediol from Crude Glycerol Using an Engineered Metabolic Pathway in *Escherichia coli*", Applied Biochemistry and Biotechnology, vol. 166, No. 7, 2012, pp. 1801-1813.
Li et al., "Cupriavidus Necator JMP134 Rapidly Reduces Furfural with a Zn-Dependent Alcohol Dehydrogenase", Biodegradation, vol. 22, No. 6, 2011, pp. 1215-1225.
Lin et al., "The BioC 0-Methyltransferase Catalyzed Methyl Esterification of Malonyl-Acyl Carrier Protein, an Essential Step in Biotin Synthesis", The Journal of Biological Chemistry, vol. 287, No. 44, Oct. 26, 2012, pp. 37010-37020.
Liu et al., "Two Novel Metal-independent Long-Chain Alkyl Alcohol Dehydrogenases From Geobacillus Thermodenitrificans NG80-2", Microbiology, vol. 155, No. 6, Mar. 3, 2009, pp, 2078-2085.
Lopez-Sanchez et al., "Tetralin-Induced and ThnR-Reguiated Aldehyde Dehydrogenase and β-Oxidation Genes in Sphingomonas Macrogolitabida Strain TFA", Applied Environmental Microbiology, vol. 76, No. 1, Jan. 2010, pp. 110-118.
Lutke-Eversloh et al., "Biochemical and Molecular Characterization of a Succinate Semialdehyde Dehydrogenase Involved in the Catabolism of 4-Hydroxybutyric Acid in Ralstonia Eutropha", FEMS Microbiology Letters, vol. 181, No. 1, Dec. 1, 1999, pp. 63-71.
Martin et al., "High-Titer Production of Monomeric Hydroxyvalerates from Levulinic Acid in Pseudomonas Putida", Journal of Biotechnology, vol. 139, No. 1, 2009, pp. 61-67.
McMahon et al., "Functional Screening and In Vitro Analysis Reveal Thioesterases with Enhanced Substrate Specificity Profiles That Improve Short-Chain Fatty Acid Production in *Escherichia coli*", Applied and Environmental Microbiology, vol. 60, No. 3, Feb. 2014, pp. 1042-1050.
Meijnen et al., "Improved p-Hydroxybenzoate Production by Engineered Pseudomonas Putida S12 by Using a Mixed-substrate Feeding Strategy", Applied Microbiology and Biotechnology, vol. 90, No. 3, 2011, pp. 885-893.
Myers et al., "Optimal Alignments in Linear Space", Bioinformatics, Computer Applications in the Biosciences, vol. 4, No. 1, 1988, pp. 11-17.
Neyfakh, Alexander A., "The Multidrug Efflux Transporter of Bacillus Subtilis is a Structural and Functional Homolog of the *Staphylococcus* NorA Protein", Antimicrobial Agents Chemotherapy, vol. 36, No. 2, Feb. 1992, pp. 484-485.
Ng et al., "Quinolone Resistance Mediated by norA: Physiologic Characterization and Relationship to flqB, a Quinolone Resistance Locus on the *Staphylococcus aureus* Chromosome", Antimicrobial Agents and Chemotherapy, vol. 38, No. 6, Jun. 1994, pp. 1345-1355.
Ohashi et al., "Continuous Production of Lactic Acid from Molasses by Perfusion Culture of Lactococcus Lactis Using a Stirred Ceramic Membrane Reactor", Journal of Bioscience and Bioengineering, vol. 87, No. 5, 1999, pp. 647-654.
International Search Report and Written Opinion in PCT/US2017/043218 dated Jan. 17, 2018.
International Preliminary Report on Patentability in PCT/US2017/043218 dated Jan. 29, 2019.

\* cited by examiner

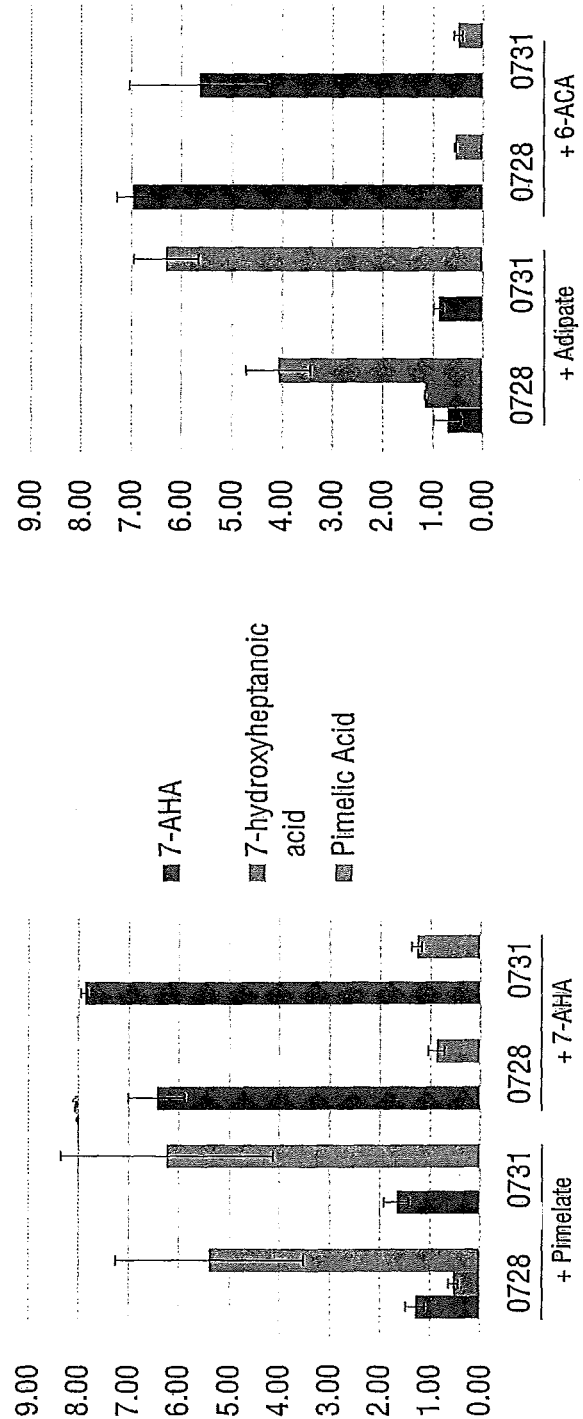
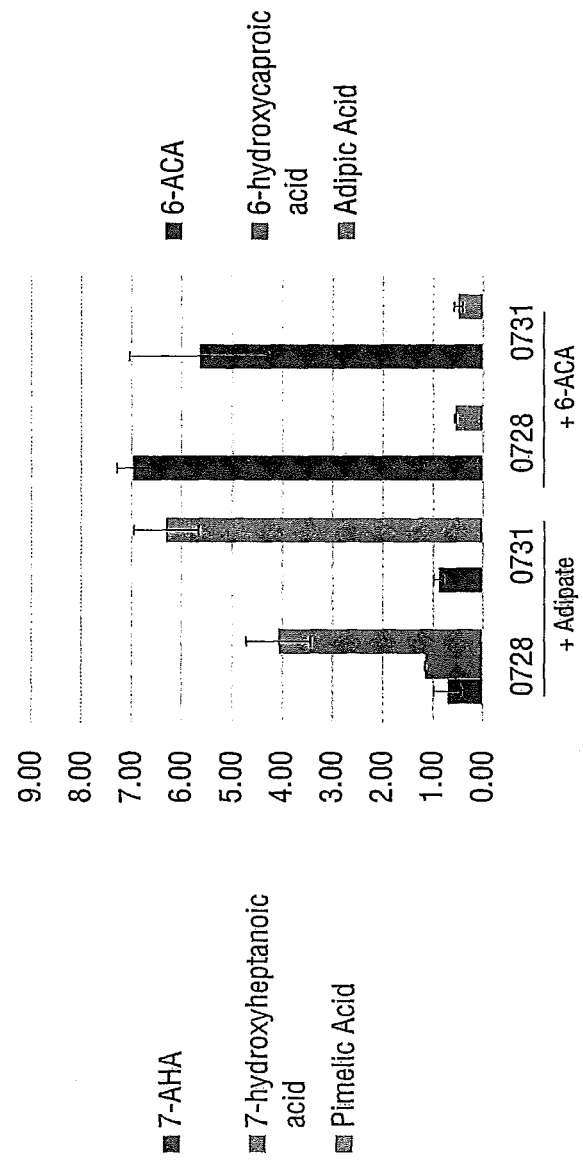
FIG. 13B
FIG. 13A

SEQUENCE LISTING

<160> NUMBER OF SEQ ID NOS: 12

<210> SEQ ID NO 1
<211> LENGTH: 1174
<212> TYPE: PRT

<213> ORGANISM: Mycobacterium marinum

<400> SEQUENCE: 1

```
Met Ser Pro Ile Thr Arg Glu Glu Arg Leu Glu Arg Ile Gln Asp
1               5                   10                  15

Leu Tyr Ala Asn Asp Pro Gln Phe Ala Ala Lys Pro Ala Thr Ala
                20                  25                  30

Ile Thr Ala Ala Ile Glu Arg Pro Gly Leu Pro Leu Pro Gln Ile Ile
            35                  40                  45

Glu Thr Val Met Thr Gly Tyr Ala Asp Arg Pro Ala Leu Ala Gln Arg
        50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
                100                 105                 110

Gly Asp Arg Val Cys Leu Leu Gly Phe Asn Ser Val Asp Tyr Ala Thr
            115                 120                 125

Ile Asp Met Thr Leu Ala Arg Leu Gly Ala Val Ala Val Pro Leu Gln
        130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
                180                 185                 190

His Arg Gln Val Asp Ala His Arg Ala Ala Val Glu Ser Ala Arg Glu
        195                 200                 205

Arg Leu Ala Gly Ser Ala Val Val Glu Thr Leu Ala Glu Ala Ile Ala
    210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
                260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
        290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
                340                 345                 350

Ser Glu Val Asp Arg Arg Leu Val Asp Gly Ala Asp Arg Val Ala Leu
            355                 360                 365

Glu Ala Gln Val Lys Ala Glu Ile Arg Asn Asp Val Leu Gly Gly Arg
        370                 375                 380

Tyr Thr Ser Ala Leu Thr Gly Ser Ala Pro Ile Ser Asp Glu Met Lys
385                 390                 395                 400
```

```
Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
        435                 440                 445

Leu Thr Asp Arg Pro His Pro Arg Gly Glu Leu Leu Val Lys Thr Asp
    450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
    530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
        595                 600                 605

Gly Ile Arg Lys Leu Ala Arg Pro Gln Leu Lys Lys His Tyr Gly Glu
    610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
        675                 680                 685

Leu Ser Phe Thr Asn Leu Leu His Glu Ile Phe Asp Ile Glu Val Pro
    690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
        755                 760                 765

Pro Arg Leu Pro Ala Ala Asn Thr Gln Val Arg Thr Val Leu Leu Thr
    770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
```

Asp Pro Glu Leu Leu Ala His Tyr Arg Ala Leu Ala Gly Asp His Leu
     820                 825                 830
                 835                 840                 845

Glu Val Leu Ala Gly Asp Lys Gly Glu Ala Asp Leu Gly Leu Asp Arg
             850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
             900                 905                 910

Ile Lys Pro Tyr Ser Tyr Thr Ser Thr Ile Gly Val Ala Asp Gln Ile
         915                 920                 925

Pro Pro Ser Ala Phe Thr Glu Asp Ala Asp Ile Arg Val Ile Ser Ala
             930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                 965                 970                 975

Pro Val Ala Val Phe Arg Cys Asp Met Ile Leu Ala Asp Thr Thr Trp
             980                 985                 990

Ala Gly Gln Leu Asn Val Pro Asp Met Phe Thr Arg Met Ile Leu Ser
             995                 1000                1005

Leu Ala Ala Thr Gly Ile Ala Pro Gly Ser Phe Tyr Glu Leu Ala
    1010                1015                1020

Ala Asp Gly Ala Arg Gln Arg Ala His Tyr Asp Gly Leu Pro Val
    1025                1030                1035

Glu Phe Ile Ala Glu Ala Ile Ser Thr Leu Gly Ala Gln Ser Gln
    1040                1045                1050

Asp Gly Phe His Thr Tyr His Val Met Asn Pro Tyr Asp Asp Gly
    1055                1060                1065

Ile Gly Leu Asp Glu Phe Val Asp Trp Leu Asn Glu Ser Gly Cys
    1070                1075                1080

Pro Ile Gln Arg Ile Ala Asp Tyr Gly Asp Trp Leu Gln Arg Phe
    1085                1090                1095

Glu Thr Ala Leu Arg Ala Leu Pro Asp Arg Gln Arg His Ser Ser
    1100                1105                1110

Leu Leu Pro Leu Leu His Asn Tyr Arg Gln Pro Glu Arg Pro Val
    1115                1120                1125

Arg Gly Ser Ile Ala Pro Thr Asp Arg Phe Arg Ala Ala Val Gln
    1130                1135                1140

Glu Ala Lys Ile Gly Pro Asp Lys Asp Ile Pro His Val Gly Ala
    1145                1150                1155

Pro Ile Ile Val Lys Tyr Val Ser Asp Leu Arg Leu Leu Gly Leu
    1160                1165                1170

Leu

<210> SEQ ID NO 2
<211> LENGTH: 1173
<212> TYPE: PRT
<213> ORGANISM: Mycobacterium smegmatis

<400> SEQUENCE: 2

Met Thr Ser Asp Val His Asp Ala Thr Asp Gly Val Thr Glu Thr Ala

-continued

```
1               5                   10                  15
Leu Asp Asp Glu Gln Ser Thr Arg Arg Ile Ala Glu Leu Tyr Ala Thr
            20                  25                  30
Asp Pro Glu Phe Ala Ala Ala Pro Leu Pro Ala Val Val Asp Ala
            35                  40                  45
Ala His Lys Pro Gly Leu Arg Leu Ala Glu Ile Leu Gln Thr Leu Phe
            50                  55                  60
Thr Gly Tyr Gly Asp Arg Pro Ala Leu Gly Tyr Arg Ala Arg Glu Leu
65                  70                  75                  80
Ala Thr Asp Glu Gly Gly Arg Thr Val Thr Arg Leu Leu Pro Arg Phe
                85                  90                  95
Asp Thr Leu Thr Tyr Ala Gln Val Trp Ser Arg Val Gln Ala Val Ala
            100                 105                 110
Ala Ala Leu Arg His Asn Phe Ala Gln Pro Ile Tyr Pro Gly Asp Ala
            115                 120                 125
Val Ala Thr Ile Gly Phe Ala Ser Pro Asp Tyr Leu Thr Leu Asp Leu
            130                 135                 140
Val Cys Ala Tyr Leu Gly Leu Val Ser Val Pro Leu Gln His Asn Ala
145                 150                 155                 160
Pro Val Ser Arg Leu Ala Pro Ile Leu Ala Glu Val Glu Pro Arg Ile
                165                 170                 175
Leu Thr Val Ser Ala Glu Tyr Leu Asp Leu Ala Val Glu Ser Val Arg
            180                 185                 190
Asp Val Asn Ser Val Ser Gln Leu Val Val Phe Asp His His Pro Glu
            195                 200                 205
Val Asp Asp His Arg Asp Ala Leu Ala Arg Ala Arg Glu Gln Leu Ala
            210                 215                 220
Gly Lys Gly Ile Ala Val Thr Thr Leu Asp Ala Ile Ala Asp Glu Gly
225                 230                 235                 240
Ala Gly Leu Pro Ala Glu Pro Ile Tyr Thr Ala Asp His Asp Gln Arg
                245                 250                 255
Leu Ala Met Ile Leu Tyr Thr Ser Gly Ser Thr Gly Ala Pro Lys Gly
            260                 265                 270
Ala Met Tyr Thr Glu Ala Met Val Ala Arg Leu Trp Thr Met Ser Phe
            275                 280                 285
Ile Thr Gly Asp Pro Thr Pro Val Ile Asn Val Asn Phe Met Pro Leu
            290                 295                 300
Asn His Leu Gly Gly Arg Ile Pro Ile Ser Thr Ala Val Gln Asn Gly
305                 310                 315                 320
Gly Thr Ser Tyr Phe Val Pro Glu Ser Asp Met Ser Thr Leu Phe Glu
                325                 330                 335
Asp Leu Ala Leu Val Arg Pro Thr Glu Leu Gly Leu Val Pro Arg Val
            340                 345                 350
Ala Asp Met Leu Tyr Gln His His Leu Ala Thr Val Asp Arg Leu Val
            355                 360                 365
Thr Gln Gly Ala Asp Glu Leu Thr Ala Glu Lys Gln Ala Gly Ala Glu
            370                 375                 380
Leu Arg Glu Gln Val Leu Gly Gly Arg Val Ile Thr Gly Phe Val Ser
385                 390                 395                 400
Thr Ala Pro Leu Ala Ala Glu Met Arg Ala Phe Leu Asp Ile Thr Leu
                405                 410                 415
Gly Ala His Ile Val Asp Gly Tyr Gly Leu Thr Glu Thr Gly Ala Val
            420                 425                 430
```

```
Thr Arg Asp Gly Val Ile Val Arg Pro Val Ile Asp Tyr Lys Leu
        435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
        595                 600                 605

Phe Ser Ala Ala Asn Gly Leu Leu Ser Gly Val Gly Lys Leu Leu Arg
    610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
        675                 680                 685

Leu Gly Gly Asp Ser Leu Ser Ala Leu Thr Leu Ser Asn Leu Leu Ser
    690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
    770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845
```

Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
                900                 905                 910

Leu Thr Glu Arg Ile Lys Pro Val Thr Tyr Leu Ser Thr Val Ser Val
                915                 920                 925

Ala Met Gly Ile Pro Asp Phe Glu Glu Asp Gly Asp Ile Arg Thr Val
            930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
                965                 970                 975

Gly Leu Pro Val Ala Thr Phe Arg Ser Asp Met Ile Leu Ala His Pro
                980                 985                 990

Arg Tyr Arg Gly Gln Val Asn Val Pro Asp Met Phe Thr Arg Leu Leu
                995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 3
<211> LENGTH: 1148
<212> TYPE: PRT
<213> ORGANISM: Segniliparus rugosus

<400> SEQUENCE: 3

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
                20                  25                  30

Ala Val Val Glu Ala Val Ser Asp Pro Ser Leu Ser Phe Thr Arg Tyr
                35                  40                  45

```
Leu Asp Thr Leu Met Arg Gly Tyr Ala Glu Arg Pro Ala Leu Ala His
 50                  55                  60

Arg Val Gly Ala Gly Tyr Glu Thr Ile Ser Tyr Gly Glu Leu Trp Ala
 65                  70                  75                  80

Arg Val Gly Ala Ile Ala Ala Ala Trp Gln Ala Asp Gly Leu Ala Pro
                 85                  90                  95

Gly Asp Phe Val Ala Thr Val Gly Phe Thr Ser Pro Asp Tyr Val Ala
                100                 105                 110

Val Asp Leu Ala Ala Ala Arg Ser Gly Leu Val Ser Val Pro Leu Gln
            115                 120                 125

Ala Gly Ala Ser Leu Ala Gln Leu Val Gly Ile Leu Glu Glu Thr Glu
130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
                180                 185                 190

Leu Ala Asp Ala Glu Glu Gln Leu Ala Arg Ala Gly Arg Ala Val Val
            195                 200                 205

Val Glu Thr Leu Ala Asp Leu Ala Ala Arg Gly Glu Ala Leu Pro Glu
210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
            275                 280                 285

Arg Ala Val Leu Ala Gly Ala Leu Ser Ala Gly Gly Thr Ala His Phe
            290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
            355                 360                 365

Pro Glu Met Arg Ala Phe Met Glu Val Leu Gly Phe Pro Leu Leu
            370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
                420                 425                 430

Ile Arg Ser Thr Ser Leu Ile Ser Gly Tyr Tyr Lys Arg Pro Glu Ile
            435                 440                 445

Thr Ala Glu Val Phe Asp Ala Gln Gly Tyr Tyr Lys Thr Gly Asp Val
450                 455                 460
```

```
Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
                500                 505                 510

Gly Asn Ser Glu Arg Ser Phe Leu Leu Ala Val Val Pro Asn Ala
            515                 520                 525

Glu Val Leu Gly Ala Arg Asp Gln Glu Ala Lys Pro Leu Ile Ala
        530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Gln Asn
                565                 570                 575

Gly Leu Leu Ser Glu Val Gly Lys Leu Leu Arg Pro Lys Leu Lys Ala
                580                 585                 590

Arg Tyr Gly Glu Ala Leu Glu Ala Arg Tyr Asp Glu Ile Ala His Gly
            595                 600                 605

Gln Ala Asp Glu Leu Arg Ala Leu Arg Asp Gly Ala Gly Gln Arg Pro
        610                 615                 620

Val Val Glu Thr Val Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
                    645                 650                 655

Ser Leu Ser Ala Leu Ser Leu Ala Asn Leu Leu His Asp Val Phe Glu
            660                 665                 670

Val Glu Val Pro Val Arg Ile Ile Ile Gly Pro Thr Ala Ser Leu Ala
                675                 680                 685

Gly Ile Ala Lys His Ile Glu Ala Glu Arg Ala Gly Ala Ser Ala Pro
        690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
                725                 730                 735

Lys Gly Leu Pro Ala Ala Asp Gln Val Arg Thr Val Leu Leu Thr Gly
            740                 745                 750

Ala Asn Gly Trp Leu Gly Arg Phe Leu Ala Leu Glu Gln Leu Glu Arg
        755                 760                 765

Leu Ala Arg Ser Gly Gln Asp Gly Gly Lys Leu Ile Cys Leu Val Arg
770                 775                 780

Gly Lys Asp Ala Ala Ala Ala Arg Arg Arg Ile Glu Glu Thr Leu Gly
785                 790                 795                 800

Thr Asp Pro Ala Leu Ala Ala Arg Phe Ala Glu Leu Ala Glu Gly Arg
                805                 810                 815

Leu Glu Val Val Pro Gly Asp Val Gly Glu Pro Lys Phe Gly Leu Asp
                820                 825                 830

Asp Ala Ala Trp Asp Arg Leu Ala Glu Glu Val Asp Val Ile Val His
            835                 840                 845

Pro Ala Ala Leu Val Asn His Val Leu Pro Tyr His Gln Leu Phe Gly
        850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
```

```
                      885                 890                 895
Val Glu Pro Ser Ser Phe Glu Glu Asp Gly Asp Ile Arg Ala Val Val
                900                 905                 910

Pro Glu Arg Pro Leu Gly Asp Gly Tyr Ala Asn Gly Tyr Gly Asn Ser
            915                 920                 925

Lys Trp Ala Gly Glu Val Leu Leu Arg Glu Ala His Glu Leu Val Gly
        930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
        995                 1000                1005

Phe Thr Ala Glu Ala Ile Thr Thr Leu Gly Ala Glu Pro Ser Trp
    1010                1015                1020

Phe Asp Gly Gly Ala Gly Phe Arg Ser Phe Asp Val Phe Asn Pro
    1025                1030                1035

His His Asp Gly Val Gly Leu Asp Glu Phe Val Asp Trp Leu Ile
    1040                1045                1050

Glu Ala Gly His Pro Ile Ser Arg Ile Asp Asp His Lys Glu Trp
    1055                1060                1065

Phe Ala Arg Phe Glu Thr Ala Val Arg Gly Leu Pro Glu Ala Gln
    1070                1075                1080

Arg Gln His Ser Leu Leu Pro Leu Leu Arg Ala Tyr Ser Phe Pro
    1085                1090                1095

His Pro Pro Val Asp Gly Ser Val Tyr Pro Thr Gly Lys Phe Gln
    1100                1105                1110

Gly Ala Val Lys Ala Ala Gln Val Gly Ser Asp His Asp Val Pro
    1115                1120                1125

His Leu Gly Lys Ala Leu Ile Val Lys Tyr Ala Asp Asp Leu Lys
    1130                1135                1140

Ala Leu Gly Leu Leu
    1145

<210> SEQ ID NO 4
<211> LENGTH: 1185
<212> TYPE: PRT
<213> ORGANISM: Mycobacterium massiliense

<400> SEQUENCE: 4

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Tyr Gly Glu Leu Trp Ser
                85                  90                  95
```

```
Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
            180                 185                 190

Phe Asp Tyr Thr Pro Glu Val Asp Asp Gln Arg Glu Ala Phe Glu Ala
        195                 200                 205

Ala Ser Thr Gln Leu Ala Gly Thr Gly Ile Ala Leu Glu Thr Leu Asp
    210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
            260                 265                 270

Arg Trp Trp Ile Arg Glu Asp Val Met Ala Gly Thr Glu Asn Leu Pro
        275                 280                 285

Met Ile Gly Leu Asn Phe Met Pro Met Ser His Ile Met Gly Arg Gly
    290                 295                 300

Thr Leu Thr Ser Thr Leu Ser Thr Gly Gly Thr Gly Tyr Phe Ala Ala
305                 310                 315                 320

Ser Ser Asp Met Ser Thr Leu Phe Glu Asp Met Glu Leu Ile Arg Pro
                325                 330                 335

Thr Ala Leu Ala Leu Val Pro Arg Val Cys Asp Met Val Phe Gln Arg
            340                 345                 350

Phe Gln Thr Glu Val Asp Arg Arg Leu Ala Ser Gly Asp Thr Ala Ser
        355                 360                 365

Ala Glu Ala Val Ala Ala Glu Val Lys Ala Asp Ile Arg Asp Asn Leu
    370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
        435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Ile Asp Arg Arg Asn
            500                 505                 510

Asn Val Leu Lys Leu Ser Gln Gly Glu Phe Val Ala Val Ala Thr Leu
```

```
            515                 520                 525
Glu Ala Glu Tyr Ala Asn Ser Pro Val Val His Gln Ile Tyr Val Tyr
    530                 535                 540
Gly Ser Ser Glu Arg Ser Tyr Leu Leu Ala Val Val Pro Thr Pro
545                 550                 555                 560
Glu Ala Val Ala Ala Ala Lys Gly Asp Ala Ala Leu Lys Thr Thr
                565                 570                 575
Ile Ala Asp Ser Leu Gln Asp Ile Ala Lys Glu Ile Gln Leu Gln Ser
                580                 585                 590
Tyr Glu Val Pro Arg Asp Phe Ile Ile Glu Pro Gln Pro Phe Thr Gln
    595                 600                 605
Gly Asn Gly Leu Leu Thr Gly Ile Ala Lys Leu Ala Arg Pro Asn Leu
    610                 615                 620
Lys Ala His Tyr Gly Pro Arg Leu Glu Gln Met Tyr Ala Glu Ile Ala
625                 630                 635                 640
Glu Gln Gln Ala Ala Glu Leu Arg Ala Leu His Gly Val Asp Pro Asp
                645                 650                 655
Lys Pro Ala Leu Glu Thr Val Leu Lys Ala Ala Gln Ala Leu Leu Gly
                660                 665                 670
Val Ser Ser Ala Glu Leu Ala Ala Asp Ala His Phe Thr Asp Leu Gly
    675                 680                 685
Gly Asp Ser Leu Ser Ala Leu Ser Phe Ser Asp Leu Leu Arg Asp Ile
    690                 695                 700
Phe Ala Val Glu Val Pro Val Gly Val Ile Val Ser Ala Ala Asn Asp
705                 710                 715                 720
Leu Gly Gly Val Ala Lys Phe Val Asp Glu Gln Arg His Ser Gly Gly
                725                 730                 735
Thr Arg Pro Thr Ala Glu Thr Val His Gly Ala Gly His Thr Glu Ile
                740                 745                 750
Arg Ala Ala Asp Leu Thr Leu Asp Lys Phe Ile Asp Glu Ala Thr Leu
    755                 760                 765
His Ala Ala Pro Ser Leu Pro Lys Ala Ala Gly Ile Pro His Thr Val
    770                 775                 780
Leu Leu Thr Gly Ser Asn Gly Tyr Leu Gly His Tyr Leu Ala Leu Glu
785                 790                 795                 800
Trp Leu Glu Arg Leu Asp Lys Thr Asp Gly Lys Leu Ile Val Ile Val
                805                 810                 815
Arg Gly Lys Asn Ala Glu Ala Ala Tyr Gly Arg Leu Glu Glu Ala Phe
                820                 825                 830
Asp Thr Gly Asp Thr Glu Leu Leu Ala His Phe Arg Ser Leu Ala Asp
    835                 840                 845
Lys His Leu Glu Val Leu Ala Gly Asp Ile Gly Asp Pro Asn Leu Gly
    850                 855                 860
Leu Asp Ala Asp Thr Trp Gln Arg Leu Ala Asp Thr Val Asp Val Ile
865                 870                 875                 880
Val His Pro Ala Ala Leu Val Asn His Val Leu Pro Tyr Asn Gln Leu
                885                 890                 895
Phe Gly Pro Asn Val Val Gly Thr Ala Glu Ile Ile Lys Leu Ala Ile
                900                 905                 910
Thr Thr Lys Ile Lys Pro Val Thr Tyr Leu Ser Thr Val Ala Val Ala
    915                 920                 925
Ala Tyr Val Asp Pro Thr Thr Phe Asp Glu Glu Ser Asp Ile Arg Leu
    930                 935                 940
```

```
Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
            965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
        995                 1000                1005

Ile Leu Ser Leu Ile Ala Thr Gly Ile Ala Pro Gly Ser Phe Tyr
1010                1015                1020

Gln Ala Gln Thr Thr Gly Glu Arg Pro Leu Ala His Tyr Asp Gly
    1025                1030                1035

Leu Pro Gly Asp Phe Thr Ala Glu Ala Ile Thr Thr Leu Gly Thr
    1040                1045                1050

Gln Val Pro Glu Gly Ser Glu Gly Phe Val Thr Tyr Asp Cys Val
    1055                1060                1065

Asn Pro His Ala Asp Gly Ile Ser Leu Asp Asn Phe Val Asp Trp
    1070                1075                1080

Leu Ile Glu Ala Gly Tyr Pro Ile Ala Arg Ile Asp Asn Tyr Thr
    1085                1090                1095

Glu Trp Phe Thr Arg Phe Asp Thr Ala Ile Arg Gly Leu Ser Glu
    1100                1105                1110

Lys Gln Lys Gln His Ser Leu Leu Pro Leu Leu His Ala Phe Glu
    1115                1120                1125

Gln Pro Ser Ala Ala Glu Asn His Gly Val Val Pro Ala Lys Arg
    1130                1135                1140

Phe Gln His Ala Val Gln Ala Ala Gly Ile Gly Pro Val Gly Gln
    1145                1150                1155

Asp Gly Thr Thr Asp Ile Pro His Leu Ser Arg Arg Leu Ile Val
    1160                1165                1170

Lys Tyr Ala Lys Asp Leu Glu Gln Leu Gly Leu Leu
    1175                1180                1185

<210> SEQ ID NO 5
<211> LENGTH: 1186
<212> TYPE: PRT
<213> ORGANISM: Segniliparus rotundus

<400> SEQUENCE: 5

Met Thr Gln Ser His Thr Gln Gly Pro Gln Ala Ser Ala Ala His Ser
1               5                   10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
```

```
              115                 120                 125
Ile Gly Phe Ile Ser Val Asp Tyr Val Ala Ile Asp Ile Ala Gly Val
        130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                    165                 170                 175

Ser Ile Glu His Leu Pro Thr Ala Val Asp Ala Val Leu Ala Thr Pro
                180                 185                 190

Ser Val Arg Arg Leu Leu Val Phe Asp Tyr Arg Ala Gly Ser Asp Glu
                195                 200                 205

Asp Arg Glu Ala Val Glu Ala Ala Lys Arg Lys Ile Ala Asp Ala Gly
        210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                    245                 250                 255

Ser Leu Ser Leu Leu Ile Tyr Thr Ser Gly Ser Thr Gly Thr Pro Lys
                260                 265                 270

Gly Ala Met Tyr Pro Glu Arg Asn Val Ala His Phe Trp Gly Gly Val
                275                 280                 285

Trp Ala Ala Ala Phe Asp Glu Asp Ala Ala Pro Pro Val Pro Ala Ile
        290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                    325                 330                 335

Asp Leu Ser Thr Leu Phe Glu Asp Leu Lys Leu Ala Arg Pro Thr Asn
                340                 345                 350

Leu Phe Leu Val Pro Arg Val Val Glu Met Leu Tyr Gln His Tyr Gln
                355                 360                 365

Ser Glu Leu Asp Arg Arg Gly Val Gln Asp Gly Thr Arg Glu Ala Glu
        370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                    405                 410                 415

Ile Glu Ser Leu Leu Gln Ile His Leu Val Asp Gly Tyr Gly Ser Thr
                420                 425                 430

Glu Ala Gly Pro Val Trp Arg Asp Gly Tyr Leu Val Lys Pro Pro Val
                435                 440                 445

Thr Asp Tyr Lys Leu Ile Asp Val Pro Glu Leu Gly Tyr Phe Ser Thr
        450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                    485                 490                 495

Glu Asp Gly Phe Tyr Leu Thr Gly Asp Val Val Ala Gln Ile Gly Pro
                500                 505                 510

Glu Gln Phe Ala Tyr Val Asp Arg Arg Lys Asn Val Leu Lys Leu Ser
                515                 520                 525

Gln Gly Glu Phe Val Thr Leu Ala Lys Leu Glu Ala Ala Tyr Ser Ser
        530                 535                 540
```

```
Ser Pro Leu Val Arg Gln Leu Phe Val Tyr Gly Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
            580                 585                 590

Ile Ala Arg Asp Glu Gly Leu Gln Ser Tyr Glu Val Pro Arg Asp Phe
            595                 600                 605

Ile Ile Glu Thr Asp Pro Phe Thr Val Glu Asn Gly Leu Leu Ser Asp
            610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Met Leu Gly Ala Ser Ala Ala Glu Ile Lys
            675                 680                 685

Pro Asp Ala His Phe Thr Asp Leu Gly Gly Asp Ser Leu Ser Ala Leu
690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
            755                 760                 765

Asp Lys Phe Ile Asp Glu Gln Thr Leu Glu Ala Ala Lys His Leu Pro
770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
            820                 825                 830

Ala Lys Ala Arg Leu Asp Ala Ala Tyr Glu Ser Gly Asp Pro Lys Leu
            835                 840                 845

Ala Gly His Tyr Gln Asp Leu Ala Ala Thr Thr Leu Glu Val Leu Ala
            850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
            900                 905                 910

Val Ala Glu Ile Ile Lys Leu Ala Ile Thr Thr Arg Ile Lys Pro Val
            915                 920                 925

Thr Tyr Leu Ser Thr Val Ala Val Ala Gly Val Glu Pro Ser Ala
            930                 935                 940

Leu Asp Glu Asp Gly Asp Ile Arg Thr Val Ser Ala Glu Arg Ser Val
945                 950                 955                 960
```

```
Asp Glu Gly Tyr Ala Asn Gly Tyr Gly Asn Ser Lys Trp Gly Gly Glu
            965                 970                 975

Val Leu Leu Arg Glu Ala His Asp Arg Thr Gly Leu Pro Val Arg Val
        980                 985                 990

Phe Arg Ser Asp Met Ile Leu Ala His Gln Lys Tyr Thr Gly Gln Val
    995                 1000                1005

Asn Ala Thr Asp Gln Phe Thr Arg Leu Val Gln Ser Leu Leu Ala
1010                1015                1020

Thr Gly Leu Ala Pro Lys Ser Phe Tyr Glu Leu Asp Ala Gln Gly
    1025                1030                1035

Asn Arg Gln Arg Ala His Tyr Asp Gly Ile Pro Val Asp Phe Thr
    1040                1045                1050

Ala Glu Ser Ile Thr Thr Leu Gly Gly Asp Gly Leu Glu Gly Tyr
    1055                1060                1065

Arg Ser Tyr Asn Val Phe Asn Pro His Arg Asp Gly Val Gly Leu
    1070                1075                1080

Asp Glu Phe Val Asp Trp Leu Ile Glu Ala Gly His Pro Ile Thr
    1085                1090                1095

Arg Ile Asp Asp Tyr Asp Gln Trp Leu Ser Arg Phe Glu Thr Ser
    1100                1105                1110

Leu Arg Gly Leu Pro Glu Ser Lys Arg Gln Ala Ser Val Leu Pro
    1115                1120                1125

Leu Leu His Ala Phe Ala Arg Pro Gly Pro Ala Val Asp Gly Ser
    1130                1135                1140

Pro Phe Arg Asn Thr Val Phe Arg Thr Asp Val Gln Lys Ala Lys
    1145                1150                1155

Ile Gly Ala Glu His Asp Ile Pro His Leu Gly Lys Ala Leu Val
    1160                1165                1170

Leu Lys Tyr Ala Asp Asp Ile Lys Gln Leu Gly Leu Leu
    1175                1180                1185

<210> SEQ ID NO 6
<211> LENGTH: 1168
<212> TYPE: PRT
<213> ORGANISM: Mycobacterium smegmatis

<400> SEQUENCE: 6

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
            20                  25                  30

Ile Ser Ala Ala Ala Ala Asp Pro Glu Leu Arg Leu Pro Ala Ala Val
        35                  40                  45

Lys Gln Ile Leu Ala Gly Tyr Ala Asp Arg Pro Ala Leu Gly Lys Arg
    50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125

Ile Ala Leu Leu Glu Leu Gly Ala Val Ser Val Pro Leu Gln Thr Ser
    130                 135                 140
```

```
Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
            165                 170                 175

Glu Ser Gly Pro Ala Pro Ser Arg Leu Val Val Phe Asp Tyr Ser His
        180                 185                 190

Glu Val Asp Asp Gln Arg Glu Ala Phe Glu Ala Ala Lys Gly Lys Leu
        195                 200                 205

Ala Gly Thr Gly Val Val Glu Thr Ile Thr Asp Ala Leu Asp Arg
210                 215                 220

Gly Arg Ser Leu Ala Asp Ala Pro Leu Tyr Val Pro Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
        275                 280                 285

Leu Asn Phe Met Pro Met Ser His Val Met Gly Arg Gly Ile Leu Cys
    290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
        355                 360                 365

Ala Val Leu Glu Glu Val Arg Thr Gln Leu Leu Gly Gly Arg Phe Val
    370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
        435                 440                 445

Asp Arg Pro Tyr Pro Arg Gly Glu Leu Leu Val Lys Ser Glu Gln Met
    450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
    530                 535                 540

Tyr Leu Leu Ala Val Val Val Pro Thr Glu Glu Ala Leu Ser Arg Trp
545                 550                 555                 560
```

```
Asp Gly Asp Glu Leu Lys Ser Arg Ile Ser Asp Ser Leu Gln Asp Ala
            565                 570                 575
Ala Arg Ala Ala Gly Leu Gln Ser Tyr Glu Ile Pro Arg Asp Phe Leu
            580                 585                 590
Val Glu Thr Thr Pro Phe Thr Leu Glu Asn Gly Leu Leu Thr Gly Ile
            595                 600                 605
Arg Lys Leu Ala Arg Pro Lys Leu Lys Ala His Tyr Gly Glu Arg Leu
            610                 615                 620
Glu Gln Leu Tyr Thr Asp Leu Ala Glu Gly Gln Ala Asn Glu Leu Arg
625                 630                 635                 640
Glu Leu Arg Arg Asn Gly Ala Asp Arg Pro Val Val Glu Thr Val Ser
            645                 650                 655
Arg Ala Ala Val Ala Leu Leu Gly Ala Ser Val Thr Asp Leu Arg Ser
            660                 665                 670
Asp Ala His Phe Thr Asp Leu Gly Gly Asp Ser Leu Ser Ala Leu Ser
            675                 680                 685
Phe Ser Asn Leu Leu His Glu Ile Phe Asp Val Asp Val Pro Val Gly
            690                 695                 700
Val Ile Val Ser Pro Ala Thr Asp Leu Ala Gly Val Ala Ala Tyr Ile
705                 710                 715                 720
Glu Gly Glu Leu Arg Gly Ser Lys Arg Pro Thr Tyr Ala Ser Val His
            725                 730                 735
Gly Arg Asp Ala Thr Glu Val Arg Ala Arg Asp Leu Ala Leu Gly Lys
            740                 745                 750
Phe Ile Asp Ala Lys Thr Leu Ser Ala Ala Pro Gly Leu Pro Arg Ser
            755                 760                 765
Gly Thr Glu Ile Arg Thr Val Leu Leu Thr Gly Ala Thr Gly Phe Leu
            770                 775                 780
Gly Arg Tyr Leu Ala Leu Glu Trp Leu Glu Arg Met Asp Leu Val Asp
785                 790                 795                 800
Gly Lys Val Ile Cys Leu Val Arg Ala Arg Ser Asp Asp Glu Ala Arg
            805                 810                 815
Ala Arg Leu Asp Ala Thr Phe Asp Thr Gly Asp Ala Thr Leu Leu Glu
            820                 825                 830
His Tyr Arg Ala Leu Ala Ala Asp His Leu Glu Val Ile Ala Gly Asp
            835                 840                 845
Lys Gly Glu Ala Asp Leu Gly Leu Asp His Asp Thr Trp Gln Arg Leu
            850                 855                 860
Ala Asp Thr Val Asp Leu Ile Val Asp Pro Ala Ala Leu Val Asn His
865                 870                 875                 880
Val Leu Pro Tyr Ser Gln Met Phe Gly Pro Asn Ala Leu Gly Thr Ala
            885                 890                 895
Glu Leu Ile Arg Ile Ala Leu Thr Thr Thr Ile Lys Pro Tyr Val Tyr
            900                 905                 910
Val Ser Thr Ile Gly Val Gly Gln Gly Ile Ser Pro Glu Ala Phe Val
            915                 920                 925
Glu Asp Ala Asp Ile Arg Glu Ile Ser Ala Thr Arg Arg Val Asp Asp
            930                 935                 940
Ser Tyr Ala Asn Gly Tyr Gly Asn Ser Lys Trp Ala Gly Glu Val Leu
945                 950                 955                 960
Leu Arg Glu Ala His Asp Trp Cys Gly Leu Pro Val Ser Val Phe Arg
            965                 970                 975
Cys Asp Met Ile Leu Ala Asp Thr Thr Tyr Ser Gly Gln Leu Asn Leu
```

```
                980             985                 990
Pro Asp Met Phe Thr Arg Leu Met  Leu Ser Leu Val Ala  Thr Gly Ile
            995                 1000                1005

Ala Pro Gly Ser Phe Tyr Glu  Leu Asp Ala Asp Gly  Asn Arg Gln
    1010                1015                1020

Arg Ala His Tyr Asp Gly Leu  Pro Val Glu Phe Ile  Ala Glu Ala
    1025                1030                1035

Ile Ser Thr Ile Gly Ser Gln  Val Thr Asp Gly Phe  Glu Thr Phe
    1040                1045                1050

His Val Met Asn Pro Tyr Asp  Asp Gly Ile Gly Leu  Asp Glu Tyr
    1055                1060                1065

Val Asp Trp Leu Ile Glu Ala  Gly Tyr Pro Val His  Arg Val Asp
    1070                1075                1080

Asp Tyr Ala Thr Trp Leu Ser  Arg Phe Glu Thr Ala  Leu Arg Ala
    1085                1090                1095

Leu Pro Glu Arg Gln Arg Gln  Ala Ser Leu Leu Pro  Leu Leu His
    1100                1105                1110

Asn Tyr Gln Gln Pro Ser Pro  Pro Val Cys Gly Ala  Met Ala Pro
    1115                1120                1125

Thr Asp Arg Phe Arg Ala Ala  Val Gln Asp Ala Lys  Ile Gly Pro
    1130                1135                1140

Asp Lys Asp Ile Pro His Val  Thr Ala Asp Val Ile  Val Lys Tyr
    1145                1150                1155

Ile Ser Asn Leu Gln Met Leu  Gly Leu Leu
    1160                1165

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
                20                  25                  30

Ala Arg Val Met Thr Arg Gly Glu Gly Val Tyr Leu Trp Asp Ser Glu
            35                  40                  45

Gly Asn Lys Ile Ile Asp Gly Met Ala Gly Leu Trp Cys Val Asn Val
        50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175
```

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455

<210> SEQ ID NO 8
<211> LENGTH: 468
<212> TYPE: PRT
<213> ORGANISM: Pseudomonas aeruginosa

<400> SEQUENCE: 8

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

```
Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Ser Thr
        115                 120                 125

Ala Val Asp Thr Ala Ile Arg Leu Met His Tyr Tyr Gln Asn Cys Arg
130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 9
<211> LENGTH: 454
<212> TYPE: PRT
<213> ORGANISM: Pseudomonas syringae
```

<400> SEQUENCE: 9

```
Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190

Gly Gly Asp Met Thr Pro Asp Glu Phe Gly Ile Trp Ala Ala Glu Gln
        195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415
```

Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
            435                 440                 445

Leu Ala Val Leu Gln Gly
        450

<210> SEQ ID NO 10
<211> LENGTH: 467
<212> TYPE: PRT
<213> ORGANISM: Rhodobacter sphaeroides

<400> SEQUENCE: 10

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala

```
                      325                 330                 335
Ala Ala Leu Ala Asn Ile Glu Leu Met Glu Arg Glu Gly Ile Val Asp
                340                 345                 350

Gln Ala Arg Glu Met Ala Asp Tyr Phe Ala Ala Leu Ala Ser Leu
            355                 360                 365

Arg Asp Leu Pro Gly Val Ala Glu Thr Arg Ser Val Gly Leu Val Gly
            370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
                420                 425                 430

Ile Ile Ser Arg Ala Gln Ile Asp Glu Met Val Ala Ile Met Arg Gln
                435                 440                 445

Ala Ile Thr Glu Val Ser Ala Ala His Gly Leu Thr Ala Lys Glu Pro
                450                 455                 460

Ala Ala Val
465

<210> SEQ ID NO 11
<211> LENGTH: 459
<212> TYPE: PRT
<213> ORGANISM: Escherichia coli

<400> SEQUENCE: 11

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
                20                  25                  30

Ala Leu Asn Arg Glu Val Ile Glu Tyr Phe Lys Glu His Val Asn Pro
            35                  40                  45

Gly Phe Leu Glu Tyr Arg Lys Ser Val Thr Ala Gly Gly Asp Tyr Gly
        50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
            115                 120                 125

Leu Ala Lys Thr Leu Ala Ala Leu Thr Pro Gly Lys Leu Lys Tyr Ser
        130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220
```

```
Cys Lys Lys Thr Gly Asp Asp Val Ala Ala Val Ile Leu Glu Pro Ile
225                 230                 235                 240

Gln Gly Glu Gly Val Ile Leu Pro Pro Gly Tyr Leu Thr Ala
            245                 250                 255

Val Arg Lys Leu Cys Asp Glu Phe Gly Ala Leu Met Ile Leu Asp Glu
        260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
        290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
        435                 440                 445

Leu Ala Ala Met Arg Val Ser Val Glu Glu Ala
        450                 455

<210> SEQ ID NO 12
<211> LENGTH: 453
<212> TYPE: PRT
<213> ORGANISM: Vibrio fluvialis

<400> SEQUENCE: 12

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140
```

-continued

```
Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
            165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Arg Glu Gly Ala Asp Thr Ile Ala Gly Phe Phe Ala Glu Pro
            210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
                260                 265                 270

Thr Tyr Asp Phe Thr Pro Asp Ala Ile Ile Ser Ser Lys Asn Leu Thr
            275                 280                 285

Ala Gly Phe Phe Pro Met Gly Ala Val Ile Leu Gly Pro Glu Leu Ser
            290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
            435                 440                 445

Phe Ala Glu Val Ala
450
```

MATERIALS AND METHODS FOR DIRECTING CARBON FLUX AND INCREASED PRODUCTION OF 7-AMINOHEPTANOIC ACID OR 6-AMINOHEXANOIC ACID

This patent application claims the benefit of priority from U.S. Provisional Application Ser. No. 62/366,597, filed Jul. 25, 2016, the contents of which are herein incorporated by reference in their entirety.

TECHNICAL FIELD

This disclosure relates to genome-scale attenuation or knockout strategies for directing carbon flux to carbon based building blocks building blocks such as, but not limited to C4 through C15 building blocks.

In one nonlimiting embodiment, this disclosure relates to genome-scale attenuation or knockout strategies for directing carbon flux to certain C7 building blocks within the 7-aminoheptanoic acid (7-AHA) biosynthesis pathway, for example, to achieve reduced flux to unwanted side products in the 7-AHA biosynthesis pathway, such as 7-hydroxyheptanoic acid and 1,7-heptanediol while achieving increased production of desired intermediates including 7-AHA, pimelic acid, and heptamethylenediamine.

In one nonlimiting embodiment, this disclosure also relates to genome-scale attenuation or knockout strategies for directing carbon flux to certain C6 building blocks within the 6-aminohexanoic acid (6-AHA) biosynthesis pathway, for example, to achieve reduced flux to unwanted side products in the 6-AHA biosynthesis pathway, such as 6-hydroxyhexanoic acid and 1,6-hexanediol while achieving increased production of desired intermediates including 6-AHA, hexanedioic acid, and hexamethylenediamine.

This disclosure also relates to non-naturally occurring mutant bacterial strains comprising one or more gene disruptions in aldehyde reductase and/or aldehyde dehydrogenase genes that are generated to direct carbon flux to C4 through C15 building blocks.

In one nonlimiting embodiment, this disclosure relates to non-naturally occurring mutant bacterial strains comprising one or more gene disruptions in aldehyde reductase and/or aldehyde dehydrogenase genes that are generated to direct carbon flux to C7 building blocks.

In one nonlimiting embodiment, this disclosure relates to non-naturally occurring mutant bacterial strains comprising one or more gene disruptions in aldehyde reductase and/or aldehyde dehydrogenase genes that are generated to direct carbon flux to C6 building blocks.

This disclosure further relates to a method for enhancing production of carbon-based chemicals such as, but not limited to, 7-AHA and 6-AHA by generating non-naturally occurring mutant bacterial strains, culturing said mutant bacterial strains in the presence of suitable substrates or under desired growth conditions, and substantially purifying the carbon-based chemical such as, but not limited to 7-AHA or 6-AHA.

BACKGROUND

Nylons are polyamides that are sometimes synthesized by the condensation polymerization of a diamine with a dicarboxylic acid. Similarly, Nylons may be produced by the condensation polymerization of lactams.

Nylon 7 is produced by polymerization of 7-aminoheptanoic acid (also known as 7-AHA), whereas Nylon 7,7 is produced by condensation polymerization of pimelic acid (also known as heptane 1,7-dioate) and heptamethylenediamine (also known as 1,7-diaminoheptane).

Both bioderived feedstocks and petrochemical feedstocks are viable starting materials for the biocatalysis processes, but no economically viable petrochemical routes exist for producing the monomers for Nylon 7 and Nylon 7,7. Given no economically viable petrochemical monomer feedstocks, biotechnology offers an alternative approach via biocatalysis. Biocatalysis is the use of biological catalysts, such as enzymes, to perform biochemical transformations of organic compounds.

Against this background, it is clear that there is a need for cost competitive, biocatalyst-based biosynthetic methods for efficiently producing "C7 building blocks," including pimelic acid, 7-aminoheptanoic acid, heptamethylenediamine, 7-hydroxyheptanoic acid, 7-aminoheptanoyl, and 1,7-heptanediol. Among these C7 building blocks, pimelic acid, 7-aminoheptanoic acid, and heptamethylenediamine are of particular interest as chemical intermediates for forming Nylon 7 and Nylon 7,7.

However, no wild-type prokaryote or eukaryote naturally overproduces or excretes C7 building blocks to the extracellular environment. The optimality principle states that microorganisms regulate their biochemical networks to support maximum biomass growth. Beyond the need to express heterologous pathways in a host organism, directing carbon flux towards C7 building blocks that serve as carbon sources rather than to biomass growth constituents contradicts the optimality principle. For example, transferring the 1-butanol pathway from *Clostridium* species into other production strains has often fallen short by an order of magnitude compared to the production performance of native producers (Shen et al., Appl. Environ. Microbiol., 77(9), 2905-2915 (2011)).

Nevertheless, the metabolism of pimelic acid has been reported. The dicarboxylic acid, pimelic acid, is converted efficiently as a carbon source by a number of bacteria and yeasts via β-oxidation into central metabolites. β-oxidation of Coenzyme A (CoA)-activated pimelate to CoA-activated 3-oxopimelate facilitates further catabolism via, for example, pathways associated with aromatic substrate degradation. The catabolism of 3-oxopimeloyl-CoA to acetyl-CoA and glutaryl-CoA by several bacteria has been characterized comprehensively (Harwood and Parales, Annual Review of Microbiology, 50, 553-590 (1996)).

The biosynthesis of C7 building blocks by recombinant host microorganisms has been described in U.S. Patent Publication Nos. 2014/0186904 and 2014/0242655.

Pimelic acid semialdehyde can be derived from pimeloyl-Coenzyme A (CoA), pimeloyl-[Acyl Carrier Protein (ACP)], pimelic acid, or α-ketosuberate. Pimeloyl-CoA and pimeloyl-[ACP] can be derived from a number of sources, including from a diverse number of naturally occurring metabolic pathways that form pimeloyl-CoA or pimeloyl-[ACP] as an intermediate in the naturally occurring metabolic pathway.

Of particular interest, the engineered pathway for 7-AHA biosynthesis in *E. coli* utilizes the biotin biosynthesis pathway for the generation of the C7 diacid intermediate, pimelyl-ACP (FIG. 1). The C7 backbone of biotin is generated via a modified fatty acid biosynthesis pathway to generate pimelyl-ACP. Pimelyl-ACP is then acted on by a series of enzymes (BioF, BioA, BioD, BioB) to generate biotin (Streit and Entcheva (2003); Lin and Cronan (2012)). The pimelyl-ACP from the biotin pathway is a key intermediate in the 7-AHA pathway. As a thioesterase (TE) (EC 3.1.2.-) releases pimelate from the ACP, the free pimelate can then be converted by the action of a carboxylic acid reductase (CAR) (EC 1.2.99.-) to the pimelic acid semialdehyde, which is in turn converted to 7-AHA by the action of ω-transaminase (co-TAM) (EC 2.6.1.-).

This pathway has been fully exemplified in *E. coli* for the production of pimelic acid and its conversion to 7-AHA (FIG. 1). However, major side products are 7-hydroxyheptanoic acid (7-HO-heptanoic acid) and 1,7-heptanediol, due to activities of endogenous *E. coli* aldehyde reductase (ALR) or alcohol dehydrogenase (EC 1.1.1.-). For example, feeding experiments with pimelic acid into recombinant host strains expressing CAR and w-TAM show that as much as 80% of pimelate is converted to these two products, while 7-AHA is a minor product with <3% yield from pimelic acid.

The biosynthesis of C6 building blocks by recombinant host microorganisms has been described in, for example, U.S. Patent Publication No. 2014/0199737.

The identification and elimination of endogenous aldehyde reductase and/or aldehyde dehydrogenase activities, individually or in combination, will enable the development of recombinant host strains for directing carbon flux to certain C4 through C15 building blocks with reduced flux to unwanted side products.

SUMMARY

This disclosure is based at least in part on the discovery that it is possible to construct biochemical pathways for producing carbon chain aliphatic backbone precursors, in which one or two functional groups, i.e., carboxyl, amine, or hydroxyl, can be formed, leading to the synthesis of one or more carbon based building blocks. Described herein are methods and genetically modified hosts that allow for more efficient use of carbon chain aliphatic backbone precursors and production of carbon based building blocks by directing flux within the carbon based building block biosynthesis pathways.

In one nonlimiting embodiment, a seven carbon chain aliphatic backbone precursor, in which one or two functional groups, i.e., carboxyl, amine, or hydroxyl, can be formed, leading to the synthesis of one or more of pimelic acid, 7-aminoheptanoate, 7-hydroxyheptanoate, heptamethylenediamine, 7-aminoheptanol, and 1,7-heptanediol ("C7 building blocks"). Described herein are methods and genetically modified hosts that allow for more efficient use of seven carbon aliphatic backbone precursors and production of C7 building blocks.

Pimelic acid and pimelate, pimelyl and pimeloyl, 7-hydroxyheptanoic acid and 7-hydroxyheptanoate, and 7-aminoheptanoic and 7-aminoheptanoate are used interchangeably herein to refer to the compound in any of its neutral or ionized forms, including any salt forms thereof. It is understood by those skilled in the art that the specific form will depend on pH.

In one nonlimiting embodiment, this disclosure is further based on directing flux within the C7 building block biosynthesis pathway, including for example the 7-AHA biosynthesis pathway, by attenuating one or more of aldehyde reductase and/or aldehyde dehydrogenase genes.

In one nonlimiting embodiment, a six carbon chain aliphatic backbone precursor, in which one or two functional groups, i.e., carboxyl, amine, or hydroxyl, can be formed, leading to the synthesis of one or more of adipic acid, 6-aminohexanoate, 6-hydroxyhexanoate, hexamethylenediamine, 6-aminohexanol, and 1,6-hexanediol ("C6 building blocks"). Described herein are methods and genetically modified hosts that allow for more efficient use of six carbon aliphatic backbone precursors and production of C6 building blocks.

Adipic acid, hexanedioic acid, 6-hydroxyhexanoic acid and 6-hydroxyhexanoate, and 6-aminohexanoic and 6-aminohexanoate are used interchangeably herein to refer to the compound in any of its neutral or ionized form's, including any salt forms thereof. It is understood by those skilled in the art that the specific form will depend on pH.

In one nonlimiting embodiment, this disclosure is further based on directing flux within the C6 building block biosynthesis pathway, including for example the 6-AHA biosynthesis pathway, by attenuating one or more of aldehyde reductase and/or aldehyde dehydrogenase genes.

For compounds containing carboxylic acid groups such as organic monoacids, hydroxyacids, aminoacids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as but not limited to organic amines, aminoacids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin.

For compounds containing both amine groups and carboxylic acid groups such as but not limited to aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, or muconic acid; or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

These pathways, metabolic engineering and cultivation strategies described herein rely on fatty acid elongation and synthesis enzymes or homologs accepting methyl-ester shielded dicarboxylic acids as substrates.

In one nonlimiting embodiment, the present disclosure provides a method for enhancing production of 7-aminoheptanoic acid comprising: a) generating a non-naturally occurring recombinant host comprising one or more gene disruptions in aldehyde reductase and/or aldehyde dehydrogenase genes, wherein the gene disruptions reduce aldehyde reductase and/or aldehyde dehydrogenase activity of polypeptides encoded by the aldehyde reductase and/or aldehyde dehydrogenase genes, and wherein the recombinant host produces an increased level of 7-aminoheptanoic acid converted from pimelic acid or pimelic acid derivatives as compared to wild-type recombinant host; b) culturing the recombinant host in the presence of a suitable substrate or metabolic intermediate and under conditions suitable for the conversion of pimelic acid or pimelic acid derivatives to 7-aminoheptanoic acid; and c) substantially purifying the 7-aminoheptanoic acid.

In one nonlimiting embodiment, the present disclosure also provides a non-naturally occurring recombinant host comprising one or more gene attenuations in aldehyde reductase and/or aldehyde dehydrogenase genes, wherein said gene attenuations reduce aldehyde reductase and/or aldehyde dehydrogenase activity of polypeptides encoded by said genes, and wherein said recombinant host produces an increased level of 7-aminoheptanoic acid converted from pimelic acid or pimelic acid derivatives as compared to wild-type recombinant host.

In some nonlimiting embodiments, the pimelic acid derivatives comprise pimelyl-ACP and pimelic acid semialdehyde.

In some nonlimiting embodiments, the level of side products other than 7-aminoheptanoic acid converted from pimelic acid or pimelic acid derivatives is reduced as compared to wild-type recombinant host.

In some nonlimiting embodiments, the side products comprise one or more members of the group consisting of 7-hydroxyheptanoic acid, 7-hydroxyheptanal, 1,7-heptanediol, 7-aminoheptanal, 7-aminoheptanol, and 1,7-diaminoheptane.

In some nonlimiting embodiments, the side products comprise one or more members of the group consisting of 7-hydroxyheptanoic acid and 1,7-heptanediol.

In one nonlimiting embodiment, the present disclosure provides a method for enhancing production of 6-aminohexanoic acid comprising: a) generating a non-naturally occurring recombinant host comprising one or more gene disruptions in aldehyde reductase and/or aldehyde dehydrogenase genes, wherein the gene disruptions reduce aldehyde reductase and/or aldehyde dehydrogenase activity of polypeptides encoded by the aldehyde reductase and/or aldehyde dehydrogenase genes, and wherein the recombinant host produces an increased level of 6-aminohexanoic acid converted from adipic acid or adipic acid derivatives as compared to wild-type recombinant host; b) culturing the recombinant host in the presence of a suitable substrate or metabolic intermediate and under conditions suitable for the conversion of adipic acid or adipic acid derivatives to 6-aminohexanoic acid; and c) substantially purifying the 6-aminohexanoic acid.

In one nonlimiting embodiment, the present disclosure also provides a non-naturally occurring recombinant host comprising one or more gene attenuations in aldehyde reductase and/or aldehyde dehydrogenase genes, wherein said gene attenuations reduce aldehyde reductase and/or aldehyde dehydrogenase activity of polypeptides encoded by said genes, and wherein said recombinant host produces an increased level of 6-aminohexanoic acid converted from adipic acid or adipic acid derivatives as compared to wild-type recombinant host.

In some nonlimiting embodiments, the adipic acid derivatives comprise adipoyl-ACP and adipic acid semialdehyde.

In some nonlimiting embodiments, the level of side products other than 6-aminohexanoic acid converted from adipic acid or adipic acid derivatives is reduced as compared to wild-type recombinant host.

In some nonlimiting embodiments, the side products comprise one or more members of the group consisting of 6-hydroxyhexanoic acid, 6-hydroxyhexanal, 1,6-hexanediol, 6-aminohexanal, 6-aminohexanol, and 1,6-diaminohexane.

In some nonlimiting embodiments, the side products comprise one or more members of the group consisting of 6-hydroxyhexanoic acid and 1,6-hexanediol.

In some nonlimiting embodiments, the gene attenuations are achieved through use of a method selected from the group consisting of transposons, homologous recombination, PCR, mutagenesis, enzyme inhibitors, antisense oligonucleotides, RNAi interference, and genome-editing technologies.

In some nonlimiting embodiments, the homologous recombination method comprises double cross-over approach.

In some nonlimiting embodiments, the PCR method comprises a one-step inactivation approach based on PCR products developed by Datsenko and Wanner.

In some nonlimiting embodiments, the genome-editing technologies comprise an approach based on CRISPR-Cas9 system or its equivalents.

In some nonlimiting embodiments, the recombinant host further comprising at least one of a polypeptide having the activity of a carboxylic acid reductase classified under EC 1.2.99.- and a polypeptide having the activity of a ω-transaminase (ω-TAM) classified under EC 2.6.1.-.

In some nonlimiting embodiments, the aldehyde reductase genes encode polypeptides having at least 60% amino acid sequence identity or homology to any one of the polypeptides having the activity of aldehyde reductases classified under EC 1.1.1.-.

In some nonlimiting embodiments, the aldehyde reductase genes encode polypeptides having at least 70% amino acid sequence identity or homology to any one of the polypeptides having the activity of aldehyde reductases classified under EC 1.1.1.-.

In some nonlimiting embodiments, the aldehyde reductase genes encode polypeptides having at least 80% amino acid sequence identity or homology to any one of the polypeptides having the activity of aldehyde reductases classified under EC 1.1.1.-.

In some nonlimiting embodiments, the aldehyde reductase genes encode polypeptides having at least 90% amino acid sequence identity or homology to any one of the polypeptides having the activity of aldehyde reductases classified under EC 1.1.1.-.

In some nonlimiting embodiments, the aldehyde reductase genes encode polypeptides having at least 95% amino acid sequence identity or homology to any one of the polypeptides having the activity of aldehyde reductases classified under EC 1.1.1.-.

In some nonlimiting embodiments, the aldehyde reductase genes encode polypeptides having at least 99% amino acid sequence identity or homology to any one of the polypeptides having the activity of aldehyde reductases classified under EC 1.1.1.-.

In some nonlimiting embodiments, the aldehyde reductase genes encode polypeptides having the activity of aldehyde reductases classified under EC 1.1.1.-.

In some nonlimiting embodiments, the aldehyde reductase genes are selected from the group consisting of adhE, yqhD, adhP, eutG, yjgB, yiaY, fucO, betA, eutE, yahK, yqhE, gldA, ybbO, and yghA.

In some nonlimiting embodiments, the aldehyde dehydrogenase genes encode polypeptides having at least 60% amino acid sequence identity or homology to any one of the polypeptides having the activity of aldehyde dehydrogenases classified under EC 1.2.1.-.

In some nonlimiting embodiments, the aldehyde dehydrogenase genes encode polypeptides having at least 70% amino acid sequence identity or homology to any one of the polypeptides having the activity of aldehyde dehydrogenases classified under EC 1.2.1.-.

In some nonlimiting embodiments, the aldehyde dehydrogenase genes encode polypeptides having at least 80% amino acid sequence identity or homology to any one of the polypeptides having the activity of aldehyde dehydrogenases classified under EC 1.2.1.-.

In some nonlimiting embodiments, the aldehyde dehydrogenase genes encode polypeptides having at least 90% amino acid sequence identity or homology to any one of the polypeptides having the activity of aldehyde dehydrogenases classified under EC 1.2.1.-.

In some nonlimiting embodiments, the aldehyde dehydrogenase genes encode polypeptides having at least 95% amino acid sequence identity or homology to any one of the polypeptides having the activity of aldehyde dehydrogenases classified under EC 1.2.1.-.

In some nonlimiting embodiments, the aldehyde dehydrogenase genes encode polypeptides having at least 99% amino acid sequence identity or homology to any one of the polypeptides having the activity of aldehyde dehydrogenases classified under EC 1.2.1.-.

In some nonlimiting embodiments, the aldehyde reductase genes encode polypeptides having the activity of aldehyde reductases classified under EC 1.1.1.-.

In some nonlimiting embodiments, the transcription of the aldehyde reductase and/or aldehyde dehydrogenase genes is induced in response to the presence of cognate substrates.

In some nonlimiting embodiments, the cognate substrates comprise at least one of the members of the group consisting of pimelic acid semialdehyde, adipic acid semialdehyde, pimelic acid semialdehyde methyl ester, and adipic acid semialdehyde methyl ester.

In some nonlimiting embodiments, the transcriptional induction of the aldehyde reductase and/or aldehyde dehydrogenase genes is identified from gene expression or transcriptomic data.

In some nonlimiting embodiments, the gene expression data is obtained from the recombinant host grown in the presence or absence of said cognate substrates.

In some nonlimiting embodiments, the transcription of the aldehyde reductase and/or aldehyde dehydrogenase genes is active under a desired growth condition.

In some nonlimiting embodiments, the aldehyde reductase and/or aldehyde dehydrogenase genes that are transcriptionally active are identified from gene expression or transcriptomic data.

In some nonlimiting embodiments, the desired growth condition comprises defined media.

In some nonlimiting embodiments, the defined media comprise glycerol as a sole carbon source.

In some nonlimiting embodiments, the aldehyde reductase and/or aldehyde dehydrogenase genes are identified by adding a cognate aldehyde substrate to the recombinant host growing in said media.

In some nonlimiting embodiments, the aldehyde reductase and/or aldehyde dehydrogenase genes are identified by adding a cognate aldehyde substrate to cell extracts from said recombinant host.

In any of these nonlimiting embodiments, the method can be performed in a recombinant host.

In any of these nonlimiting embodiments, the recombinant host can be subjected to a cultivation strategy under aerobic, anaerobic, micro-aerobic or mixed oxygen/denitrification cultivation conditions.

In any of these nonlimiting embodiments, the recombinant host can be cultured under conditions of nutrient limitation.

In any of these nonlimiting embodiments, the recombinant host can be retained using a ceramic hollow fiber membrane to maintain a high cell density during fermentation.

In any of these nonlimiting embodiments, the principal carbon source fed to the fermentation can be derived from biological or non-biological feedstocks.

In some nonlimiting embodiments, the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

In some nonlimiting embodiments, the non-biological feedstock is, or derives from, natural gas, syngas, CO2/H2, methanol, ethanol, benzoate, non-volatile residue (NVR) caustic wash waste stream from cyclohexane oxidation processes, or terephthalic acid/isophthalic acid mixture waste streams.

In some nonlimiting embodiments, the recombinant host is a prokaryote.

In some nonlimiting embodiments, the prokaryote is from the genus *Escherichia Escherichia* such as *Escherichia coli Escherichia coli*; from the genus *Clostridium* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia acidovorans*, from the genus *Bacillus* such as *Bacillus subtillis; from the genes Lactobacillus* such as *Lactobacillus delbrueckii*; from the genus *Lactococcus* such as *Lactococcus lactis* or from the genus *Rhodococcus* such as *Rhodococcus equi*.

In some nonlimiting embodiments, the recombinant host is *Escherichia coli*.

In some nonlimiting embodiments, the recombinant host is a eukaryote.

In some nonlimiting embodiments, the eukaryote is from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

In any of these nonlimiting embodiments, the recombinant host's tolerance to high concentrations of a carbon based building block is improved through continuous cultivation in a selective environment.

In some nonlimiting embodiments, the recombinant host comprises one or more of the following attenuated enzymes: polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the NADH or NADPH imbalance, an glutamate dehydrogenase dissipating the NADH or NADPH imbalance, a NADH/NADPH-utilizing glutamate dehydrogenase, a pimeloyl-CoA dehydrogenase; an acyl-CoA dehydrogenase accepting carbon based building blocks and central precursors as substrates; a glutaryl-CoA dehydrogenase; or a pimeloyl-CoA synthetase.

In some nonlimiting embodiments, the recombinant host overexpresses one or more genes encoding: an acetyl-CoA synthetase, a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a L-alanine dehydrogenase; a L-glutamate dehydrogenase specific to the NADH or NADPH used to generate a co-factor imbalance; a methanol dehydrogenase, a formaldehyde dehydrogenase, a diamine transporter; a dicarboxylate transporter; an S-adenosylmethionine synthetase and/or a multidrug transporter.

The present disclosure also relates to nucleic acid constructs and expression vectors useful in these methods and recombinant hosts.

In some nonlimiting embodiments, the nucleic acid construct or expression vector comprises a polynucleotide encoding a polypeptide having carboxylate reductase activity, wherein the polynucleotide is operably linked to one or more heterologous control sequences that direct production of the polypeptide and wherein the polypeptide having carboxylate reductase activity is selected from the group consisting of: (a) a polypeptide having at least 70% sequence identity or homology to the polypeptide of SEQ ID NO: 1; (b) a polypeptide having at least 70% sequence identity or homology to the polypeptide of SEQ ID NO: 2; (c) a polypeptide having at least 70% sequence identity or homology to the polypeptide of SEQ ID NO: 3; (d) a polypeptide having at least 70% sequence identity or homology to the polypeptide of SEQ ID NO: 4; (e) a polypeptide having at least 70% sequence identity or homology to the polypeptide of SEQ ID NO: 5; and (f) a polypeptide having at least 70% sequence identity or homology to the polypeptide of SEQ ID NO: 6.

In some nonlimiting embodiments, the nucleic acid construct or expression vector comprises a polynucleotide encoding a polypeptide having ω-transaminase activity, wherein the polynucleotide is operably linked to one or more heterologous control sequences that direct production of the polypeptide and wherein the polypeptide having ω-transaminase activity is selected from the group consisting of: (a) a polypeptide having at least 70% sequence identity or homology to the polypeptide of SEQ ID NO: 7; (b) a polypeptide having at least 70% sequence identity or homology to the polypeptide of SEQ ID NO: 8; (c) a polypeptide having at least 70% sequence identity or homology to the polypeptide of SEQ ID NO: 9; (d) a polypeptide having at least 70% sequence identity or homology to the polypeptide of SEQ ID NO: 10; (e) a polypeptide having at least 70% sequence identity or homology to the polypeptide of SEQ ID NO: 11; and (f) a polypeptide having at least 70% sequence identity or homology to the polypeptide of SEQ ID NO: 12.

The present disclosure also relates to compositions comprising the nucleic acid construct or expression vector of the foregoing comprising a polynucleotide encoding a polypeptide having carboxylate reductase activity or a polynucleotide encoding a polypeptide having ω-transaminase activity.

The present disclosure also relates to a non-naturally occurring biochemical network comprising a 5-hydroxypentanoyl-CoA, an exogenous nucleic acid encoding a polypeptide having the activity of a β-ketothiolase classified under EC. 2.3.1, and a 3-oxo-7-hydroxyheptanoyl-CoA.

The present disclosure also relates to bio-derived, bio-based or fermentation-derived products comprising:

i. a composition comprising at least one bio-derived, bio-based or fermentation-derived compound produced or biosynthesized according to the methods and recombinant hosts disclosed herein, or any one of FIGS. 1-5 or FIG. 12, or any combination thereof, ii. a bio-derived, bio-based or fermentation-derived polymer comprising the bio-derived, bio-based or fermentation-derived composition or compound of i., or any combination thereof, iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof, iv. a molded substance obtained by molding the bio-derived, bio-based or fermentation-derived polymer of ii. or the bio-derived, bio-based or fermentation-derived resin of iii., or any combination thereof, v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived molded substance of iv, or any combination thereof, or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

The details of one or more nonlimiting embodiments of the invention are set forth in the accompanying drawings and the description below. Other features, objects, and advantages of the invention will be apparent from the description and the drawings, and from the claims. It is to be understood that the foregoing general description and the following detailed description are exemplary and explanatory only, and are intended to provide further, nonlimiting explanation of the disclosure.

DESCRIPTION OF DRAWINGS

FIG. 13A and FIG. 13B are bar graphs of the quantitative results of assessment of by-product formation via aldehyde dehydrogenase activity in C7 (FIG. 13A) and C6 building blocks (FIG. 13B).

DETAILED DESCRIPTION

Figure 1:
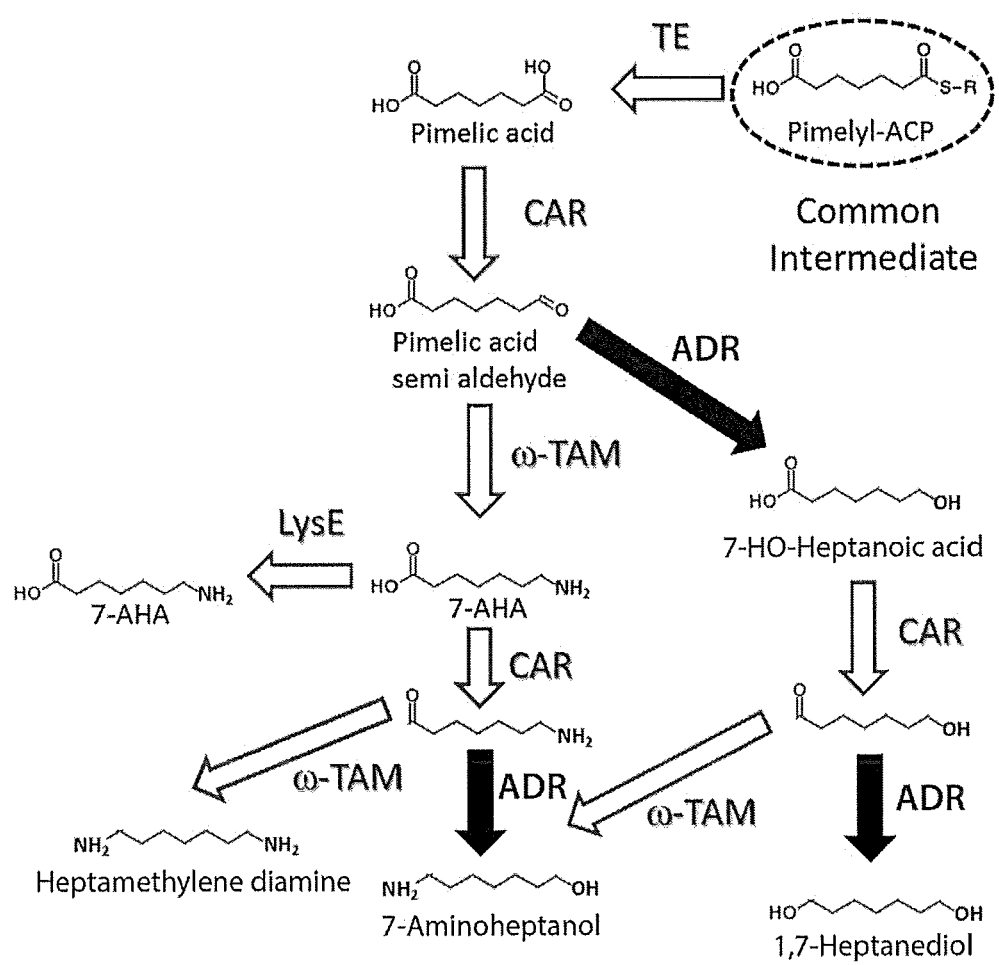
FIG. 1 is a schematic showing the conversion of pimelic acid to 7-AHA to heptamethylenediamine, along with the generation of various side products (7-hydroxyheptanoic acid and 1,7-heptanediol) by the action of aldehyde reductase (ALR), denoted by solid arrows.

In general, this disclosure provides enzymes, non-natural pathways, cultivation strategies, feedstocks, host microorganisms, and attenuations to the host's biochemical network for increased production of one or more carbon based building blocks.

By carbon based building blocks it is meant carbon chain aliphatic backbone precursors, in which one or two functional groups, i.e., carboxyl, amine, or hydroxyl, can be formed. In one nonlimiting embodiment, the backbone comprises 4 to 15 carbons. In one nonlimiting embodiment, the backbone comprises 6 or 7 carbons.

As used herein, the term "central precursor" is used to denote any metabolite in any metabolic pathway shown herein leading to the synthesis of a carbon based building block.

In one nonlimiting embodiment, this disclosure provides enzymes, non-natural pathways, cultivation strategies, feedstocks, host microorganisms, and attenuations to the host's biochemical network for increased production of one or more of pimelic acid, 7-aminoheptanoic acid, or heptamethylenediamine along with reduced production of one or more of 7-hydroxyheptanoate or 1,7-heptanediol, all of which are referred to as "C7 building blocks" herein.

In one nonlimiting embodiment, this disclosure provides enzymes, non-natural pathways, cultivation strategies, feedstocks, host microorganisms, and attenuations to the host's biochemical network for increased production of one or more of adipic acid, 6-aminohexanoic acid, or hexamethylenediamine along with reduced production of one or more of 6-hydroxyhexanoate or 1,6-hexanediol, all of which are referred to as "C6 building blocks" herein.

Host microorganisms described herein can include endogenous pathways that can be manipulated such that selected C7 or C7 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The twin "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally occurring nucleic acid is considered to be exogenous to a host once in the host. It is important to note that non-naturally occurring nucleic acids can contain nucleic acid subsequences or fragments of nucleic acid sequences that are found in nature, provided the nucleic acid as a whole does not exist in nature. For example, a nucleic acid molecule containing a genomic DNA sequence within an expression vector is a non-naturally occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be a non-naturally occurring nucleic acid. It follows that genomic DNA fragments produced by PCR or restriction endonuclease treatment as well as cDNAs are considered to be non-naturally occurring nucleic acids since they exist as separate molecules not found in nature. It also follows that any nucleic acid containing a promoter sequence and polypeptide-encoding sequence (e.g., cDNA or genomic DNA) in an arrangement not found in nature is a non-naturally occurring nucleic acid. A nucleic acid that is naturally occurring can be exogenous to a particular host microorganism. For example, an entire chromosome isolated from a cell of yeast x is an exogenous nucleic acid with respect to a cell of yeast once that chromosome is introduced into a cell of yeast.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, polypeptides having the activity of one or more of the following enzymes may be expressed in the host: a β-ketothiolase, a synthase, a 3-hydroxyacyl-CoA dehydrogenase, a 3-oxoacyl-CoA reductase, an enoyl-CoA hydratase, a trans-2-enoyl-CoA reductase, a thioesterase, a CoA transferase, an aldehyde dehydrogenase, a monooxygenase, an alcohol dehydrogenase, a 6-oxohexanoate dehydrogenase, a 7-oxoheptanoate dehydrogenase, a ω-transaminase, a 6-hydroxyhexanoate dehydrogenase, a 5-hydroxypentanoate dehydrogenase, a 4-hydroxybutyrate dehydrogenase, a carboxylate reductase, a deacylase, an N-acetyl transferase, a glutamate synthase, a 2-oxoglutarate decarboxylase, a branch-chain decarboxylase, a glutamate decarboxylase, an esterase, or an alcohol O-acetyltransferase. In recombinant hosts expressing a carboxylate reductase, a phosphopantetheinyl transferase also can be expressed as it enhances activity of the carboxylate reductase. In recombinant hosts expressing a monooxygenase, an electron transfer chain protein such as an oxidoreductase or ferredoxin polypeptide also can be expressed.

A thioesterase (TE) used in this disclosure can be any one of the following:

| Designation | | Organism |
|---|---|---|
| F9ULU3 | TE2 | Lactobacillus plantarum |
| Q39514 | TE3 | Cuphea hookeriana |
| M1WJV0 | TE4 | Desulfovibrio piezophilus |
| Q03SR8 | TE5 | Lactobacillus brevis |
| Q048X3 | TE6 | Lactobacillus delbrueckii |

-continued

| Designation | | Organism |
|---|---|---|
| C5WH65 | TE7 | Streptococcus dysgalactiae |
| Q0TM32 | TE8 | Clostridium perfringens |
| F5YA29 | TE9 | Treponema azotonutricium |
| N9VXF4 | TE10 | Clostridium hathewayi |
| F7Z1I0 | TE11 | Bacillus coagulans |
| CAE80300 | TE12 | Bdellovibrio bacteriovorus |
| M2CWP1 | TE13 | Treponema denticola |
| G4HNN3 | TE14 | Paenibacillus lactis |
| AAC49179.1 | TE15 | Cuphea palustris* |
| AAC49001.1* | TE16 | Umbellularia californica* |
| P49851 | TE17 | Bacillus subtilis YkhA |
| Q45061 | TE18 | Bacillus subtilis YNEP |
| P14205 | TE19 | Bacillus subtilis COMA2 |

For example, a recombinant host producing 7-hydroxyheptanoate can include polypeptides having the activity of one or more of the following exogenous enzymes: a monooxygenase, an alcohol dehydrogenase, a 5-oxovalerate dehydrogenase, a 6-hydroxyhexanoate dehydrogenase, a 7-oxoheptanoate dehydrogenase, a 6-oxohexanoate dehydrogenase, or an aldehyde dehydrogenase, and can further produce pimelic acid. For example, a recombinant host producing 7-hydroxyheptanoate can include polypeptides having the activity of an exogenous monooxygenase and produce pimelic acid. For example, a recombinant host producing 7-hydroxyheptanoate can include polypeptides having the activity of an exogenous 6-hydroxyhexanoate dehydrogenase and polypeptides having the activity of an aldehyde dehydrogenase, and produce pimelic acid. For example, a recombinant host producing 7-hydroxyheptanoate can include polypeptides having the activity of an exogenous alcohol dehydrogenase and polypeptides having the activity of one of the following exogenous enzymes: a 5-oxovalerate dehydrogenase, a 6-oxohexanoate dehydrogenase, or a 7-oxoheptanoate dehydrogenase, and produce pimelic acid.

For example, a recombinant host producing 7-hydroxyheptanoate or 6-hydroxyhexanoate can include polypeptides having the activity of one or more of the following exogenous enzymes: a primary alcohol dehydrogenase, an aldehyde dehydrogenase, a 6-hydroxyhexanoate dehydrogenase, or a transaminase, and further produce 7-aminoheptanoate or 6-aminohexanoate. For example, a recombinant host producing 7-hydroxyheptanoate or 6-hydroxyhexanoate can include polypeptides having the activity of an exogenous primary alcohol dehydrogenase and/or aldehyde dehydrogenase and polypeptides having the activity of an exogenous transaminase, and produce 7-aminoheptanoate or 6-aminohexanoate. For example, a recombinant host producing 7-hydroxyheptanoate or 6-hydroxyhexanoate can include polypeptides having the activity of an exogenous 6-hydroxyhexanoate dehydrogenase and polypeptides having the activity of an exogenous transaminase, and produce 7-aminoheptanoate or 6-aminohexanoate.

For example, a recombinant host producing 7-hydroxyheptanoate or 6-hydroxyhexanoate can include polypeptides having the activity of one or more of the following exogenous enzymes: a carboxylate reductase, a ω-transaminase, a deacylase, an N-acetyl transferase, or a primary alcohol dehydrogenase and/or aldehyde dehydrogenase, and produce heptamethylenediamine or hexamethylenediamine. For example, a recombinant host producing 7-hydroxyheptanoate or 6-hydroxyhexanoate can include polypeptides having the activity of an exogenous carboxylate reductase, polypeptides having the activity of an exogenous primary alcohol dehydrogenase and/or aldehyde dehydrogenase, and polypeptides having the activity of one or more exogenous transaminases (e.g., one transaminase or two different transaminases), and produce heptamethylenediamine or hexamethylenediamine. For example, a recombinant host producing 7-hydroxyheptanoate or 6-hydroxyhexanoate can include polypeptides having the activity of an exogenous carboxylate reductase and polypeptides having the activity of one or more exogenous transaminases (e.g., one transaminase or two different transaminases), and produce heptamethylenediamine or hexamethylenediamine. For example, a recombinant host producing 7-hydroxyheptanoate or 6-hydroxyhexanoate can include polypeptides having the activity of an exogenous primary alcohol dehydrogenase and/or aldehyde dehydrogenase, polypeptides having the activity of an exogenous carboxylate reductase, and polypeptides having the activity of one or more exogenous transaminases (e.g., one transaminase, or two or three different transaminases) and produce heptamethylenediamine or hexamethylenediamine. For example, a recombinant host producing 7-hydroxyheptanoate or 6-hydroxyhexanoate can include polypeptides having the activity of an exogenous primary alcohol dehydrogenase and/or aldehyde dehydrogenase, polypeptides having the activity of an exogenous N-acetyl transferase, polypeptides having the activity of a carboxylate reductase, polypeptides having the activity of a deacylase, and polypeptides having the activity of one or more exogenous transaminases (e.g., one transaminase or two different transaminases), and produce heptamethylenediamine or hexamethylenediamine.

For example, a recombinant host producing 7-hydroxyheptanoate or 6-hydroxyhexanoate can include polypeptides having the activity of one or more of the following exogenous enzymes: a carboxylate reductase and an exogenous primary alcohol dehydrogenase and/or aldehyde dehydrogenase, and further produce 1,7-heptanediol or 1,6-hexanediol.

Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank, EMBL, ExPASy, or BRENDA.

Any of the polypeptides having the activity of enzymes described herein that can be used for production of one or more carbon based building blocks, specifically C4 to C15 building blocks, more specifically C7 or C6 building blocks, or in the regulation of the biosynthesis of carbon based building blocks, can have at least 70% sequence identity or homology (e.g., at least 75%, 80%, 85%, 90%, 95%, 97%, 98%, 99%, or 100%) to the amino acid sequence of the corresponding polypeptides having the activity of wild-type enzyme. It will be appreciated that the sequence identity or homology can be determined on the basis of the polypeptides having the activity of mature enzyme (e.g., with any signal sequence removed).

A polypeptide having a certain percent (e.g., at least 75%, 80%, 85%, 90%, 95%, 97%, 98%, 99%, or 100%) of sequence identity or homology with another sequence means that, when aligned, that percentage of bases or amino acid residues is the same in comparing the two sequences.

Any of the polypeptides having the activity of enzymes described herein that can be used for production of one or more carbon based building blocks, specifically C4 to C15 building blocks, more specifically C7 or C6 building blocks can have at least 70% sequence identity or homology (e.g., at least 75%, 80%, 85%, 90%, 91%, 92%, 93%, 94%, 95%, 96%, 97%, 98%, 99%, or 100%) to the amino acid sequence of the polypeptides having the activity of corresponding wild-type enzyme. It will be appreciated that the sequence identity can be determined on the basis of the polypeptides having the activity of the mature enzyme (e.g., with any signal sequence removed) or on the basis of the polypeptides having the activity of the immature enzyme (e.g., with any signal sequence included). It also will be appreciated that the initial methionine residue may or may not be present on any of the enzyme sequences described herein.

For example, polypeptides having the activity of a carboxylate reductase described herein can have at least 70% sequence identity or homology (e.g., at least 75%, 80%, 85%, 90%, 91%, 92%, 93%, 94%, 95%, 96%, 97%, 98%, 99%, or 100%) to the amino acid sequence of polypeptides having the activity of a *Mycobacterium marinum* (see Genbank Accession No. ACC40567.1, SEQ ID NO: 1), a *Mycobacterium smegmatis* (see Genbank Accession No. ABK71854.1, SEQ ID NO: 2), a *Segniliparus rugosus* (see Genbank Accession No. EFV11917.1, SEQ ID NO: 3), a *Mycobacterium abscessus* subsp. *bolletii* (see Genbank Accession No. EIV11143.1, SEQ ID NO: 4), a *Segniliparus rotundus* (see Genbank Accession No. ADG98140.1, SEQ ID NO: 5), or a *Mycobacterium smegmatis* (see Genbank Accession No. ABK75684.1, SEQ ID NO: 6) carboxylate reductase.

For example, polypeptides having the activity of a ω-transaminase described herein can have at least 70% sequence identity or homology (e.g., at least 75%, 80%, 85%, 90%, 91%, 92%, 93%, 94%, 95%, 96%, 97%, 98%, 99%, or 100%) to the amino acid sequence of polypeptides having the activity of a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12) ω-transaminase. Some of these polypeptides having the activity of ω-transaminases are polypeptides having the activity of diamine ω-transaminases.

The percent identity and homology between two amino acid sequences can be determined as follows. First, the amino acid sequences are aligned using the BLAST 2 Sequences (B12seq) program from the stand-alone version of BLASTZ containing BLASTP version 2.0.14. This stand-alone version of BLASTZ can be obtained from the U.S. government's National Center for Biotechnology Information website (ncbi with the extension .nlm.nih.gov of the world wide web). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq1 .txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length polypeptide amino acid sequence followed by multiplying the resulting value by 100. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution and this process results in "sequence homology" of, e.g., at least 75%, 80%, 85%, 90%, 91%, 92%, 93%, 94%, 95%, 96%, 97%, 98%, or 99%. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer. Applic. Biol. Sci.,* 1988, 4, 11-17, e.g., as implemented in the program PC/GENE (Intelligenetics, Mountain View, Calif., USA). This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Such programs may include the GCG Pileup program, FASTA (Pearson et al., *Proc. Natl. Acad. Sci. USA,* 1988, 85, 2444-2448), and BLAST (BLAST Manual, Altschul et al., Nat'l Cent. Biotechnol. Inf., Nat'l Lib. Med. (NCIB NLM NIH), Bethesda, Md., and Altschul et al., NAR, 1997, 25, 3389-3402). Another alignment program is ALIGN Plus (Scientific and Educational Software, Pa.), using default parameters. Another sequence software program that finds use is the TFASTA Data Searching Program available in the Sequence Software Package Version 6.0 (Genetics Computer Group, University of Wisconsin, Madison, Wis.).

It will be appreciated that a number of nucleic acids can encode a polypeptide having a particular amino acid sequence. The degeneracy of the genetic code is well known to the art, i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the disclosure. The term "functional fragment" as used herein refers to a peptide fragment of a protein that has at least 25% (e.g., at least 30%, 40%, 50%, 60%, 70%, 75%, 80%, 85%, 90%, 95%, 98%, 99%, 100%, or even greater than 100%) of the activity of the corresponding mature, full-length, wild-type protein. The functional fragment can generally, but not always, be comprised of a continuous region of the protein, wherein the region has functional activity.

This disclosure also provides (i) functional variants of the enzymes used in the methods of the disclosure and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine, and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Any substitution of one member of the above-mentioned polar, basic, or acidic groups by another member of the same group can be deemed a conservative substitution. By contrast, a non-conservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example, a sequence used for purification of the recombinant protein (e.g., FLAG, polyhistidine (e.g., hexahistidine), hemagglutinin (HA), glutathione-S-transferase (GST), or maltose-binding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation, or ER or Golgi apparatus retention signals. Heterologous sequences can be of varying length and, in some cases, can be longer sequences than the full-length target proteins to which the heterologous sequences are attached.

Engineered hosts can naturally express none or some (e.g., one or more, two or more, three or more, four or more, five or more, or six or more) of the polypeptides having the activity of the enzymes of the pathways described herein. Thus, a pathway within an engineered host can include polypeptides having the activity of all exogenous enzymes, or can include both polypeptides having the activity of endogenous and polypeptides having the activity of exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein, recombinant hosts can include nucleic acids encoding polypeptides having the activity of one or more of a β-ketothiolase, a synthase, an esterase, an O-acetyltransferase, a CoA transferase, a CoA ligase, a dehydrogenase, a decarboxylase, a reductase, a hydratase, a thioesterase, a monooxygenase, a thioesterase, and a transaminase as described herein.

In addition, the production of carbon based building blocks in accordance with the present invention can be performed in vitro using the isolated polypeptides having the activity of the enzymes described herein, using a lysate (e.g., a cell lysate) from a host microorganism as a source of the enzymes, or using a plurality of lysates from different host microorganisms as the source of the enzymes.

The reactions of the pathways described herein can be performed in one or more host strains (a) naturally expressing polypeptides having the activity of one or more relevant enzymes, (b) genetically engineered to express polypeptides having the activity of one or more relevant enzymes, or (c) naturally expressing polypeptides having the activity of one or more relevant enzymes and genetically engineered to express polypeptides having the activity of one or more relevant enzymes. Alternatively, polypeptides having the activity of relevant enzymes can be extracted from one of the above types of host cells and used in a purified or semi-purified form. Moreover, such extracts include lysates (e.g., cell lysates) that can be used as sources of polypeptides having the activity of relevant enzymes. In the methods provided by the disclosure, all the steps can be performed in host cells, all the steps can be performed using extracted polypeptides having the activity of enzymes, or some of the steps can be performed in cells and others can be performed using extracted polypeptides having the activity of enzymes.

Figure 2:
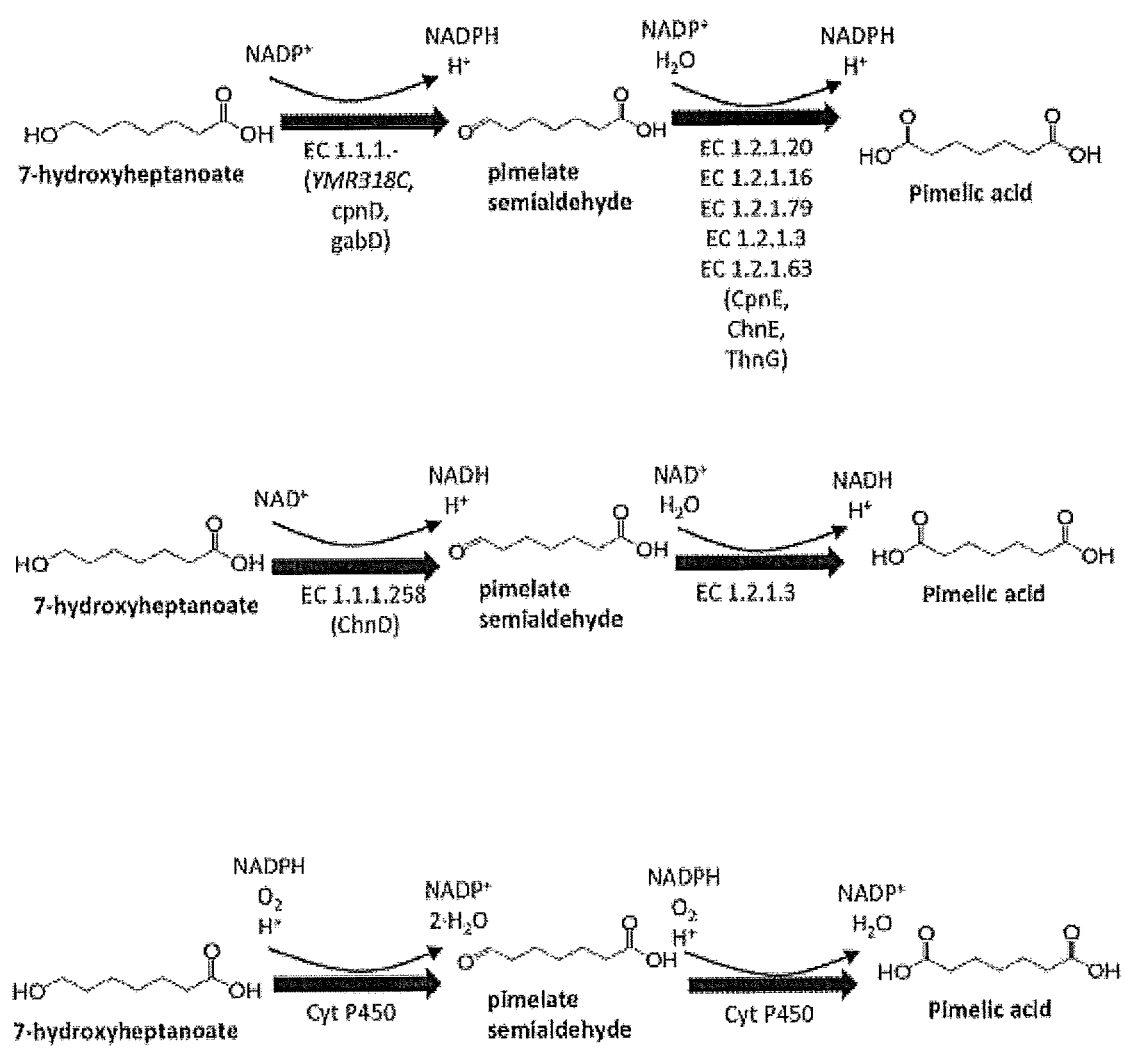
FIG. 2 is a schematic of exemplary biochemical pathways leading to pimelic acid using 7-hydroxyheptanoate as a central precursor.

Enzymes Generating the Terminal Carboxyl Groups in the Biosynthesis of Pimelic Acid or Adipic Acid As depicted in FIG. 2, a terminal carboxyl group leading to the production of pimelic acid can be enzymatically formed using polypeptides having the activity of one or more enzymes such as an aldehyde dehydrogenase, a succinate-semialdehyde dehydrogenase, a 5-oxovalerate dehydrogenase, a 6-oxohexanoate dehydrogenase, a 7-oxoheptanoate dehydrogenase, or a monooxygenase.

In some embodiments, the second terminal carboxyl group leading to the synthesis of pimelic acid can be enzymatically formed in pimelate semialdehyde by polypeptides having the activity of an aldehyde dehydrogenase classified under EC 1.2.1.3 (Guerrillot & Vandecasteele, Eur. J. Biochem., 81, 185-192 (1977)). See FIG. 2.

In some embodiments, the second terminal carboxyl group leading to the synthesis of pimelic acid is enzymatically formed in pimelate semialdehyde by polypeptides having the activity of a dehydrogenase classified under EC 1.2.1.-, such as a glutarate semialdehyde dehydrogenase classified, for example, under EC 1.2.1.20, such as the gene product of CpnE, or a 6-oxohexanoate dehydrogenase classified, for example, under EC 1.2.1.63, such as the gene product of ChnE from *Acinetobacter* sp. or a 7-oxoheptanoate dehydrogenase, such as the gene product of ThnG from *Sphingomonas macrogolitabida* (Iwaki et al., Appl. Environ. Microbiol., 65(11), 5158-5162 (1999); Lopez-Sanchez et al., Appl. Environ. Microbiol., 76(1), 110-118 (2010)). See FIG. 2.

In some embodiments, the second terminal carboxyl group leading to the synthesis of pimelic acid is enzymatically formed in pimelate semialdehyde by polypeptides having the activity of a monooxygenase in the cytochrome P450 family such as CYP4F3B (see, e.g., Sanders et al., J. Lipid Research, 46(5):1001-1008 (2005); Sanders et al., The FASEB Journal, 22(6):2064-2071 (2008)). See FIG. 2.

Figure 12:
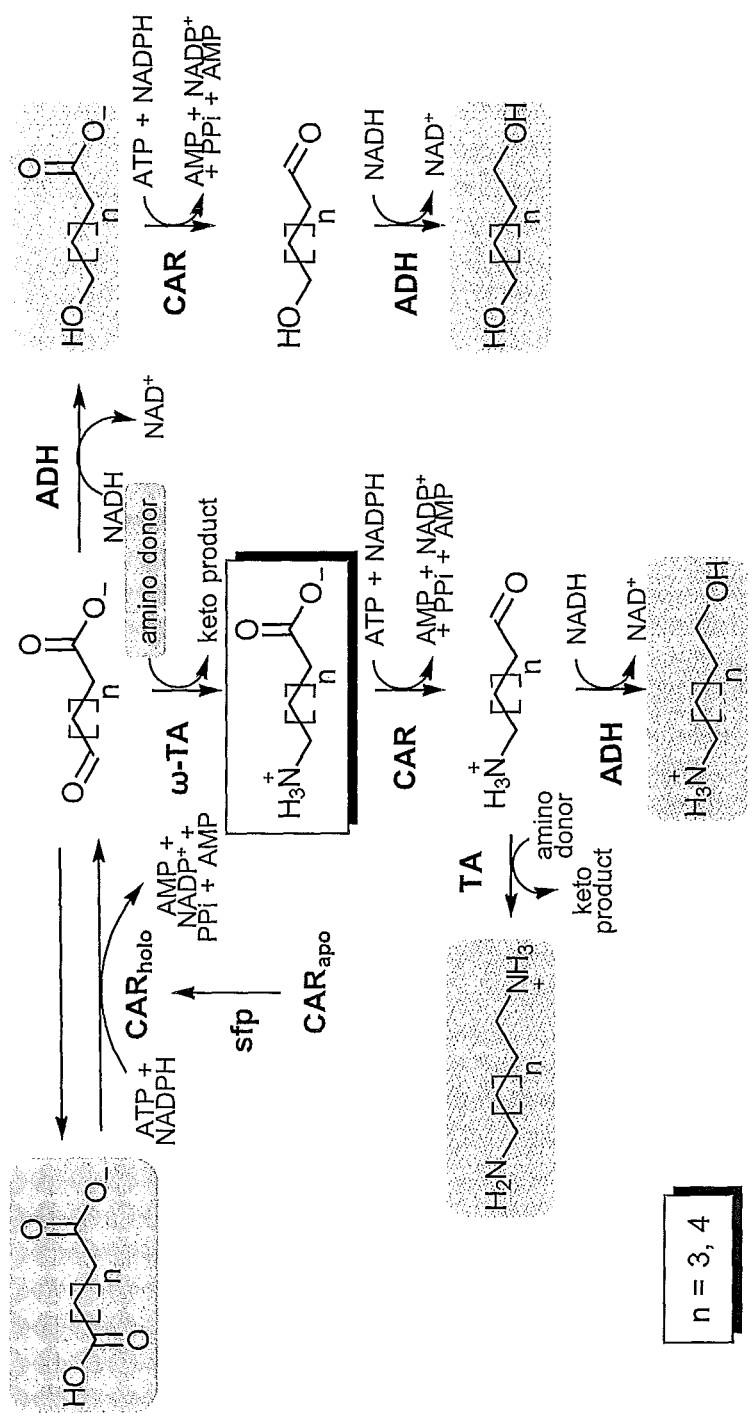
FIG. 12 is a schematic showing an overview of the downstream pathway of C6 building block production.

A similar pathway is depicted in FIG. 12 for production of C6 building blocks.

Figure 3:
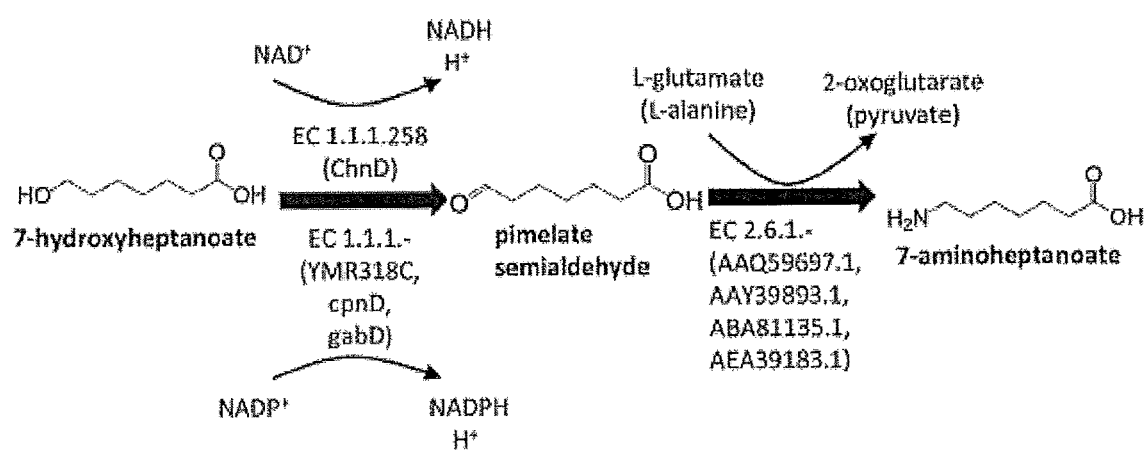
FIG. 3 is a schematic of an exemplary biochemical pathway leading to 7-AHA using 7-hydroxyheptanoate as a central precursor.
Figure 4:
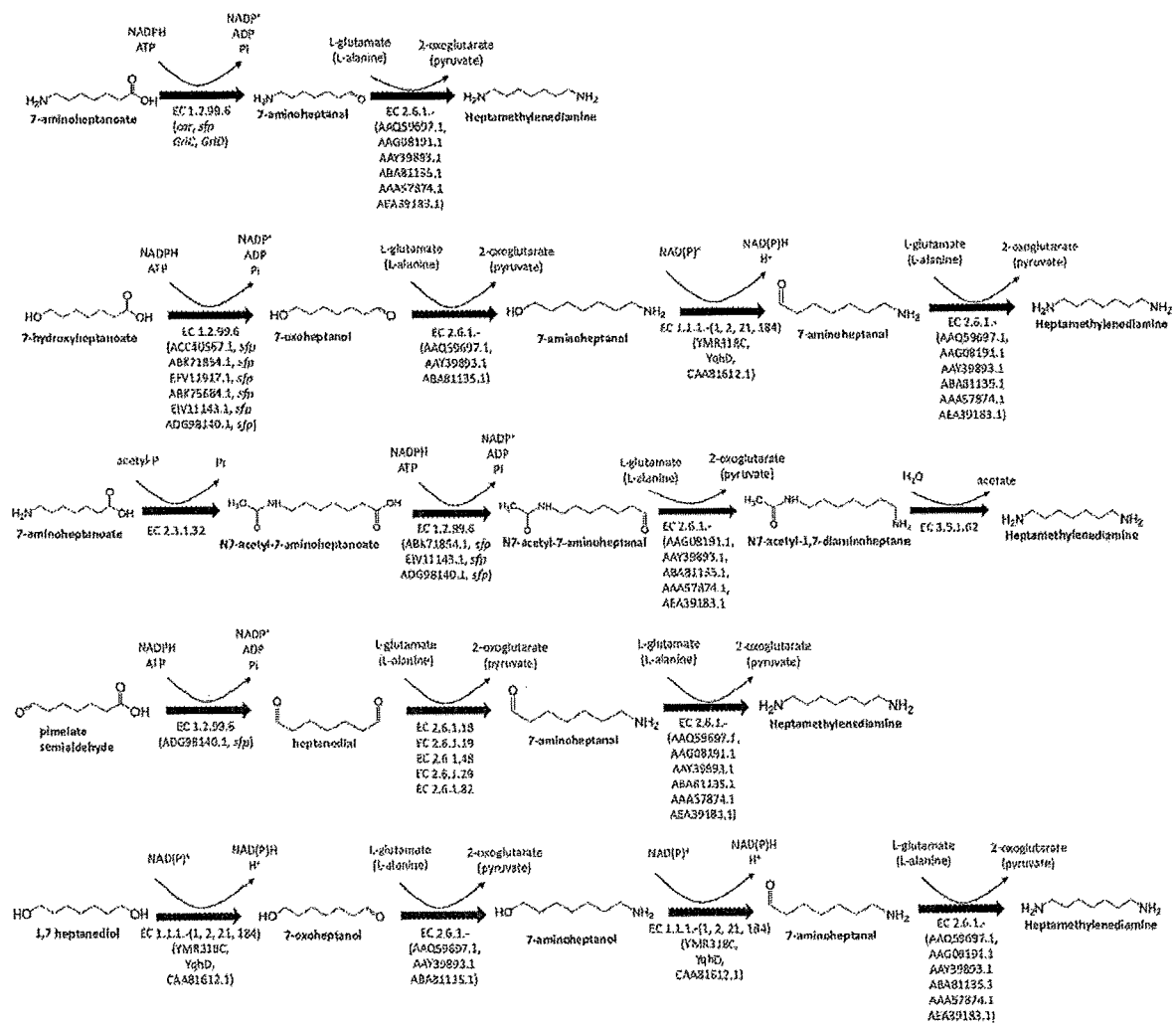
FIG. 4 is a schematic of exemplary biochemical pathways leading to heptamethylenediamine using 7-AHA, 7-hydroxyheptanoate, pimelate semialdehyde, or 1,7-heptanediol as a central precursor.

Enzymes Generating the Terminal Amine Groups in the Biosynthesis of Heptamethylenediamine or 7-Aminoheptanoate or Hexamethylenediamine or 6-Aminohexanoate As depicted in FIG. 3 and FIG. 4, terminal amine groups can be enzymatically formed using polypeptides having the activity of one or more enzymes such as a ω-transaminase or a deacylase.

In some embodiments, a terminal amine group leading to the synthesis of 7-aminoheptanoic acid is enzymatically formed in pimelate semialdehyde by polypeptides having the activity of a ω-transaminase classified, for example, under EC 2.6.1.-, e.g., EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio fluvialis* (Genbank Accession No. AEA39183.1, SEQ ID NO: 12), *Streptomyces griseus*, or *Clostridium viride*. Some of the ω-transaminases classified, for example, under EC 2.6.1.29 or EC 2.6.1.82 are diamine ω-transaminases (e.g., SEQ ID NO: 11). See FIG. 3.

The reversible ω-transaminase from *Chromobacterium violaceum* (Genbank Accession No. AAQ59697.1, SEQ ID NO: 7) has demonstrated analogous activity accepting 7-aminoheptanoic acid as an amino donor, thus forming the first terminal amine group in pimelate semialdehyde (Kaulmann et al., Enzyme and Microbial Technology, 41, 628-637 (2007)).

The reversible 4-aminobutyrate, 2-oxoglutarate transaminase from *Streptomyces griseus* has demonstrated activity for the conversion of 7-aminoheptanoate to pimelate semialdehyde (Yonaha et al., Eur. J. Biochem., 146, 101-106 (1985)).

The reversible 5-aminovalerate transaminase from *Clostridium viride* has demonstrated activity for the conversion of 7-aminoheptanoate to pimelate semialdehyde (Barker et al., J. Biol. Chem., 262(19), 8994-9003 (1987)).

In some embodiments, the second terminal amine group leading to the synthesis of heptamethylenediamine is enzymatically fainted in 7-aminoheptanal by polypeptides having the activity of a diamine transaminase classified, for example, under EC 2.6.1.29 or classified, for example, under EC 2.6.1.82, such as the gene product of YgjG from *E. coli* (Genbank Accession No. AAA57874.1, SEQ ID NO: 11). The transaminases classified under EC 2.6.1.18, EC 2.6.1.19, or EC 2.6.1.48 also can be used to synthesize heptamethylenediamine. For example, polypeptides having the activity of the transaminases set forth in SEQ ID NOs: 7-10 and 12 also can be used to produce heptamethylenediamine. See FIG. 4.

The gene product of ygjG accepts a broad range of diamine carbon chain-length substrates, such as putrescine, cadaverine, and spermidine (Samsonova et al., BMC Microbiology, 3:2 (2003)).

The diamine transaminase from *E. coli* strain B has demonstrated activity for 1,7-di aminoheptane (Kim, The Journal of Chemistry, 239(3), 783-786 (1964)).

In some embodiments, the second terminal amine group leading to the synthesis of heptamethylenediamine is enzymatically formed in N7-acetyl-1,7-diaminoheptane by polypeptides having the activity of a deacylase classified, for example, under EC 3.5.1.62 such as an acetylputrescine deacylcise.

A similar pathway is depicted in FIG. 12 for production of C6 building blocks.

Figure 5:
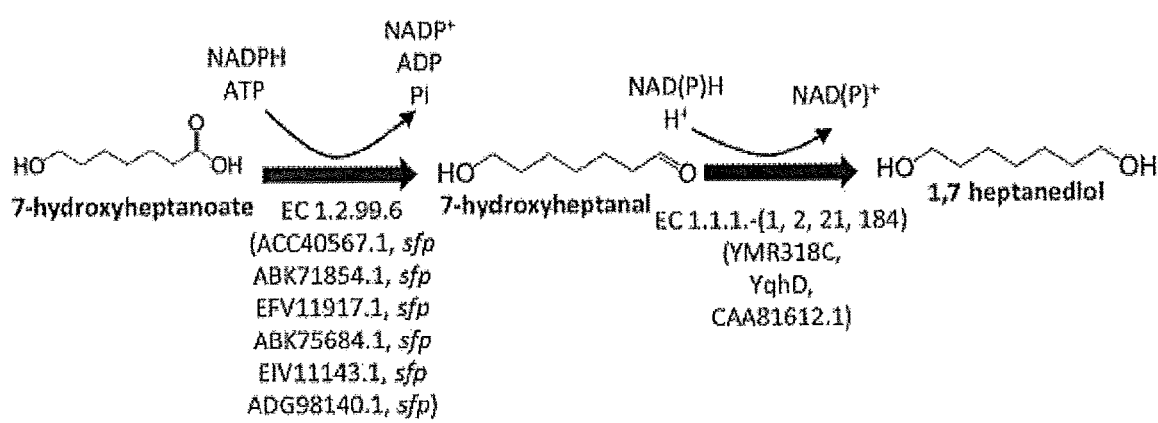
FIG. 5 is a schematic of an exemplary biochemical pathway leading to 1,7-heptanediol using 7-hydroxyheptanoate as a central precursor.

Enzymes Generating the Terminal Hydroxyl Groups in the Biosynthesis of 1,7-Heptanediol or 1,6-Hexanediol As depicted in FIG. 5, the terminal hydroxyl group can be enzymatically formed using polypeptides having the activity of one or more enzymes such as an alcohol dehydrogenase. For example, the second terminal hydroxyl group leading to the synthesis of 1,7-heptanediol can be enzymatically formed in 7-hydroxyheptanal by polypeptides having the activity of an alcohol dehydrogenase classified under EC 1.1.1.- (e.g., EC 1.1.1.1, 1.1.1.2, 1.1.1.21, or 1.1.1.184) such as the gene product of YMR318C or YqhD (Liu et al., Microbiology, 155, 2078-2085 (2009); Larroy et al., Biochem. J., 361(Pt. 1), 163-172 (2002); Jarboe, Appl. Microbiol. Biotechnol., 89(2), 249-257 (2011)), or the protein having GenBank Accession No. CAA81612.1.

A similar pathway is depicted in FIG. 12 for production of C6 building blocks.

Biochemical Pathways

Pathways Using 7-Hydroxyheptanoate as a Central Precursor to Pimelic Acid or 6-Hydroxyhexanoate to Adipic Acid In some embodiments, pimelic acid is synthesized from 7-hydroxyheptanoate by conversion of 7-hydroxyheptanoate to pimelate semialdehyde by polypeptides having the activity of an alcohol dehydrogenase classified under EC 1.1.1.- such as the gene product of YMR318C (classified, for example, under EC 1.1.1.2, see Genbank Accession No. CAA90836.1) (Larroy et al., Biochem J., 361(Pt. 1), 163-172 (2002)), cpnD (Iwaki et al., Appl. Environ. Microbiol., 68(11):5671-5684 (2002)), or gab D (Lutke-Eversloh & Steinbuchel, FEMS Microbiology Letters, 181(1):63-71 (1999)), or a 7-hydroxyheptanoate dehydrogenase classified, for example, under EC 1.1.1.258 such as the gene product of ChnD (Iwaki et al., Appl. Environ. Microbiol, 65(11):5158-5162 (1999)); followed by conversion of pimelate semialdehyde to pimelic acid by polypeptides having the activity of a dehydrogenase classified, for example, under EC 1.2.1.- such as a 7-oxoheptanoate dehydrogenase (e.g., the gene product of ThnG), a 6-oxohexanoate dehydrogenase (e.g., the gene product of ChnE), an aglutarate semialdehyde dehydrogenase classified, for example, under EC 1.2.1.20, a 5-oxovalerate dehydrogenase such as the gene product of CpnE, or an aldehyde dehydrogenase classified under EC 1.2.1.3. See FIG. 2. The alcohol dehydrogenase encoded by YMR318C has broad substrate specificity, including the oxidation of C7 alcohols.

In some embodiments, pimelic acid is synthesized from the central precursor, 7-hydroxyheptanoate, by conversion of 7-hydroxyheptanoate to pimelate semialdehyde by polypeptides having the activity of a cytochrome P450 (Sanders et al., J. Lipid Research, 46(5), 1001-1008 (2005); Sanders et al., The FASEB Journal, 22(6), 2064-2071 (2008)); followed by conversion of pimelate semialdehyde to pimelic acid by polypeptides having the activity of a monooxygenase in the cytochrome P450 family such as CYP4F3B. See FIG. 2.

A similar pathway is depicted in FIG. 12 for production of C6 building blocks.

Pathway Using 7-Hydroxyheptanoate or 6-Hydroxyhexanoate as a Central Precursor to 7-Aminoheptanoate or 6-Aminohexanoate In some embodiments, 7-aminoheptanoate is synthesized from the central precursor, 7-hydroxyheptanoate, by conversion of 7-hydroxyheptanoate to pimelate semialdehyde by polypeptides having the activity of an alcohol dehydrogenase classified, for example, under EC 1.1.1.2 such as the gene product of YMR318C; a 7-hydroxyheptanoate dehydrogenase classified, for example, under EC 1.1.1.258 such as the gene product of chnD; a 5-hydroxypentanoate dehydrogenase classified, for example, under EC 1.1.1.- such as the gene product of cpnD; or a 4-hydroxybutyrate dehydrogenase classified, for example, under EC 1.1.1.- such as the gene product of gabD; followed by conversion of pimelate semialdehyde to 7-aminoheptanoate by a ω-transaminase (EC 2.6.1.18, EC 2.6.1.19, EC 2.6.1.29, EC 2.6.1.48, or EC 2.6.1.82 such as one of SEQ ID NOs: 7-10 or 12, see above). See FIG. 3.

A similar pathway is depicted in FIG. 12 for production of C6 building blocks.

Pathway Using 7-Aminoheptanoate, 7-Hydroxyheptanoate, Pimelate Semialdehyde, or 1,7-Heptanediol as a Central Precursor to Heptamethylenediamine or 6-Aminohexanoate, 6-Hydroxyhexanoate, Adipilate Semialdehyde, or 1,6-Hexanediol as a Central Precursor to Hexamethylenediamine In some embodiments, heptamethylenediamine is synthesized from the central precursor, 7-aminoheptanoate, by conversion of 7-aminoheptanoate to 7-aminoheptanal by polypeptides having the activity of a carboxylate reductase classified, for example, under EC 1.2.99.6 such as the gene product of CAR in combination with a phosphopantetheine transferase enhancer (e.g., encoded by an sfp gene from *Bacillus subtilis* or an npt gene from *Nocardia*), or the gene products of GriC and GriD from *Streptomyces griseus* (Suzuki et al., J. Antibiot., 60(6), 380-387 (2007)); followed by conversion of 7-aminoheptanal to heptamethylenediamine by polypeptides having the activity of an ω-transaminase (e.g., EC 2.6.1.18, EC 2.6.1.19, EC 2.6.1.48, or EC 2.6.1.82 such as SEQ ID NOs: 7-12). The carboxylate reductase can be obtained, for example, from *Mycobacterium marinum* (Genbank Accession No. ACC40567.1, SEQ ID NO: 2), *Mycobacterium smegmatis* (Genbank Accession No. ABK71854.1, SEQ ID NO: 3), *Segniliparus rugosus* (Genbank Accession No. EFV11917.1, SEQ ID NO: 4), *Mycobacterium massiliense* (Genbank Accession No. EIV11143.1, SEQ ID NO: 5), *Segniliparus rotundus* (Genbank Accession No. ADG98140.1, SEQ ID NO: 6), or *Mycobacterium smegmatis* (Genbank Accession No. ABK75684.1, SEQ ID NO: 29). See FIG. 4.

The carboxylate reductase encoded by the gene product of CAR and enhancer npt (SEQ ID NO: 14) or sfp (SEQ ID NO: 13) has broad substrate specificity, including terminal difunctional C4 and C5 carboxylic acids (Venkitasubramanian et al., Enzyme and Microbial Technology, 42, 130-137 (2008)).

In some embodiments, heptamethylenediamine is synthesized from the central precursor, 7-hydroxyheptanoate, by conversion of 7-hydroxyheptanoate to 7-hydroxyheptanal (7-oxoheptanol) by polypeptides having the activity of a carboxylate reductase classified, for example, under EC 1.2.99.6 such as the gene product of CAR (see above) in combination with polypeptides having the activity of a phosphopantetheine transferase enhancer (e.g., encoded by an sfp gene from *Bacillus subtilis* or an npt gene from *Nocardia*), or the gene product of GriC and GriD (Suzuki et al. (2007), supra); followed by conversion to 7-aminoheptanol by polypeptides having the activity of an ω-transaminase classified, for example, under EC 2.6.1.18, EC 2.6.1.19, EC 2.6.1.29, EC 2.6.1.48, or EC 2.6.1.82 such as SEQ ID NOs: 7-12, see above; followed by conversion to 7-aminoheptanal by polypeptides having the activity of an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD (Liu et al., Microbiology, 155, 2078-2085 (2009); Larroy et al., Biochem. J., 361(Pt. 1), 163-172 (2002); Jarboe, Appl. Microbiol. Biotechnol., 89(2), 249-257 (2011)), or the protein having GenBank Accession No. CAA81612.1; followed by conversion to heptamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs: 7-12, see above. See FIG. 4.

In some embodiments, heptamethylenediamine is synthesized from the central precursor, 7-aminoheptanoate, by conversion of 7-aminoheptanoate to N7-acetyl-7-aminoheptanoate by polypeptides having the activity of an N-acetyltransferase such as a lysine N-acetyltransferase classified, for example, under EC 2.3.1.32; followed by conversion to N7-acetyl-7-aminoheptanal by polypeptides having the activity of a carboxylate reductase classified, for example, under EC 1.2.99.6 such as the gene product of CAR (see above, e.g., SEQ ID NO: 4, 5, or 6) in combination with polypeptides having the activity of a phosphopantetheine transferase enhancer (e.g., encoded by an sfp gene from *Bacillus subtilis* or an npt gene from *Nocardia*) or the gene product of GriC & GriD; followed by conversion to N7-acetyl-1,7-diaminoheptane by polypeptides having the activity of an ω-transaminase classified, for example, under EC 2.6.1.18, EC 2.6.1.19, EC 2.6.1.29, EC 2.6.1.48, or EC 2.6.1.82 such as SEQ ID NOs: 7-12, see above; followed by conversion to heptamethylenediamine by polypeptides having the activity of an acetyl putrescine deacylase classified, for example, under EC 3.5.1.62. See FIG. 4.

In some embodiments, heptamethylenediamine is synthesized from the central precursor, pimelate semialdehyde, by conversion of pimelate semialdehyde to heptanedial by polypeptides having the activity of a carboxylate reductase classified, for example, under EC 1.2.99.6 such as the gene product of CAR (see above, e.g., SEQ ID NO: 6) in combination with polypeptides having the activity of a phosphopantetheine transferase enhancer (e.g., encoded by an sfp gene from *Bacillus subtilis* or an npt gene from *Nocardia*), or the gene product of GriC & GriD; followed by conversion to 7-aminoheptanal by a ω-transaminase classified, for example, under EC 2.6.1.18, EC 2.6.1.19, EC 2.6.1.29, EC 2.6.1.48, or EC 2.6.1.82; followed by conversion to heptamethylenediamine by polypeptides having the activity of an ω-transaminase classified, for example, under EC 2.6.1.18, EC 2.6.1.19, EC 2.6.1.29, EC 2.6.1.48, or EC 2.6.1.82 such as SEQ ID NOs: 7-12. See FIG. 4.

In some embodiments, heptamethylenediamine is synthesized from 1,7-heptanediol by conversion of 1,7-heptanediol to 7-hydroxyheptanal using polypeptides having the activity of an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD, or the protein having GenBank Accession No. CAA81612.1; followed by conversion to 7-aminoheptanol by polypeptides having the activity of an ω-transaminase classified, for example, under EC 2.6.1.18, EC 2.6.1.19, EC 2.6.1.29, EC 2.6.1.48, or EC 2.6.1.82 such as SEQ ID NOs: 7-12; followed by conversion to 7-aminoheptanal by polypeptides having the activity of an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD, or the protein having GenBank Accession No. CAA81612.1; followed by conversion to heptamethylenediamine by polypeptides having the activity of an ω-transaminase classified, for example, under EC 2.6.1.18, EC 2.6.1.19, EC 2.6.1.29, EC 2.6.1.48, or EC 2.6.1.82 such as SEQ ID NOs: 7-12. See FIG. 4.

A similar pathway is depicted in FIG. 12 for production of C6 building blocks.

Pathways Using 7-Hydroxyheptanoate or 6-Hydroxyhexanoate as a Central Precursor to 1,7-Heptanediol or 1,6-Hexanediol In some embodiments, 1,7-heptanediol is synthesized from the central precursor, 7-hydroxyheptanoate, by conversion of 7-hydroxyheptanoate to 7-hydroxyheptanal by polypeptides having the activity of a carboxylate reductase classified, for example, under EC 1.2.99.6 such as the gene product of CAR (see above, e.g., SEQ ID NO: 2, 3, 4, 5, 6, or 16) in combination with polypeptides having the activity of a phosphopantetheine transferase enhancer (e.g., encoded by an sfp gene from *Bacillus subtilis* or an npt gene from *Nocardia*), or the gene products of GriC and GriD from *Streptomyces griseus* (Suzuki et al., J. Antibiot., 60(6), 380-387 (2007)); followed by conversion of 7-hydroxyheptanal to 1,7-heptanediol by polypeptides having the activity of an alcohol dehydrogenase (classified, for example, under EC 1.1.1.- such as EC 1.1.1.1, EC 1.1.1.2, EC 1.1.1.21, or EC 1.1.1.184) such as the gene product of YMR318C or YqhD (from *E. coli*, GenBank Accession No. AAA69178.1) (see, e.g., Liu et al., Microbiology, 155, 2078-2085 (2009); Larroy et al., Biochem. J., 361(Pt. 1), 163-172 (2002); or Jarboe, Appl. Microbiol. Biotechnol., 89(2), 249-257 (2011)), or the protein having GenBank Accession No. CAA81612.1 (from *Geobacillus stearothermophilus*). See FIG. 5.

A similar pathway is depicted in FIG. 12 for production of C6 building blocks.

Cultivation Strategy

In some embodiments, one or more carbon based building blocks are biosynthesized in a recombinant host using anaerobic, aerobic, or micro-aerobic cultivation conditions. A non-cyclical or a cyclical cultivation strategy can be used to achieve the desired cultivation conditions. For example, a non-cyclical strategy can be used to achieve anaerobic, aerobic, or micro-aerobic cultivation conditions.

In some embodiments, a cyclical cultivation strategy can be used to alternate between anaerobic cultivation conditions and aerobic cultivation conditions.

In some embodiments, the cultivation strategy entails a nutrient limitation such as a nitrogen, phosphate, or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more carbon based building blocks can derive from biological or non-biological feedstocks.

In some embodiments, the biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida,* and *Yarrowia lipolytica* (Lee et al., Appl. Biochem. Biotechnol., 166:1801-1813 (2012); Yang et al., Biotechnology for Biofuels, 5:13 (2012); Meijnen et al., Appl. Microbiol. Biotechnol., 90:885-893 (2011)).

The efficient catabolism of lignocellulosic-derived levulinic acid has been demonstrated in several organisms such as *Cupriavidus* necator and *Pseudomonas putida,* in the synthesis of 3-hydroxyvalerate via the precursor propanoyl-CoA (Jaremko and Yu, 2011, supra; Martin and Prather, J. Biotechnol., 139:61-67 (2009)).

The efficient catabolism of lignin-derived aromatic compounds such as benzoate analogues, has been demonstrated in several microorganisms such as *Pseudomonas putida* and *Cupriavidus necator* (Bugg et al., Current Opinion in Biotechnology, 22, 394-400 (2011); Perez-Pantoja et al., FEMS Microbiol. Rev., 32, 736-794 (2008)).

The efficient utilization of agricultural waste, such as olive mill waste water, has been demonstrated in several microorganisms, including *Yarrowia lipolytica* (Papanikolaou et al., Bioresour. Technol., 99(7):2419-2428 (2008)).

The efficient utilization of fermentable sugars such as monosaccharides and disaccharides derived from cellulosic, hemicellulosic, cane and beet molasses, cassava, corn, and other agricultural sources has been demonstrated for several microorganisms such as *Escherichia coli, Corynebacterium glutamicum, Lactobacillus delbrueckii,* and *Lactococcus lactis* (see, e.g., Hermann et al., J. Biotechnol., 104:155-172 (2003); Wee et al., Food Technol. Biotechnol., 44(2):163-172 (2006); Ohashi et al., J. Bioscience and Bioengineering, 87(5):647-654 (1999)).

The efficient utilization of furfural, derived from a variety of agricultural lignocellulosic sources, has been demonstrated for *Cupriavidus necator* (Li et al., Biodegradation, 22:1215-1225 (2011)).

In some embodiments, the non-biological feedstock can be, or can derive from, natural gas, syngas, CO2/H2, methanol, ethanol, benzoate, non-volatile residue (NVR), or a caustic wash waste stream from cyclohexane oxidation processes, or terephthalic acid/isophthalic acid mixture waste streams.

The efficient catabolism of methanol has been demonstrated for the methylotrophic yeast *Pichia pastoris.*

The efficient catabolism of ethanol has been demonstrated for *Clostridium kluyveri* (Seedorf et al., Proc. Natl. Acad. Sci. USA, 105(6) 2128-2133 (2008)).

The efficient catabolism of CO2 and H2, which may be derived from natural gas and other chemical and petrochemical sources, has been demonstrated for *Cupriavidus necator* (Prybylski et al., Energy, Sustainability and Society, 2:11 (2012)).

The efficient catabolism of syngas has been demonstrated for numerous microorganisms, such as *Clostridium ljung-dahlii* and *Clostridium autoethanogenum* (Kopke et al., Applied and Environmental Microbiology, 77(15):5467-5475 (2011)).

The efficient catabolism of the non-volatile residue waste stream from cyclohexane processes has been demonstrated for numerous microorganisms, such as *Delftia acidovorans* and *Cupriavidus necator* (Ramsay et al., Applied and Environmental Microbiology, 52(1):152-156 (1986)).

In some embodiments, the host microorganism is a prokaryote. For example, the prokaryote can be a bacterium from the genus *Escherichia* such as *Escherichia coli*; from the genus Clostridia such as *Clostridium ljungdahlii, Clostridium autoethanogenum,* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida,* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis.* Such prokaryotes also can be a source of genes to construct recombinant host cells described herein that are capable of producing one or more C7 or C6 building blocks.

In some embodiments, the host microorganism is a eukaryote. For example, the eukaryote can be a filamentous fungus, e.g., one from the genus *Aspergillus* such as *Aspergillus niger.* Alternatively, the eukaryote can be a yeast, e.g., one from the genus *Saccharomyces* such as *Saccharomyces cerevisiae*, from the genus *Pichia* such as *Pichia pastoris,* or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis.* Such eukaryotes also can be a source of genes to construct recombinant host cells described herein that are capable of producing one or more C7 or C6 building blocks.

Metabolic Engineering

The present disclosure provides methods involving less than all the steps described for all the above pathways. Such methods can involve, for example, one, two, three, four, five, six, seven, eight, nine, ten, 11, 12, or more of such steps. Where less than all the steps are included in such a method, the first, and in some embodiments the only, step can be any one of the steps listed.

Furthermore, recombinant hosts described herein can include any combination of the above polypeptides having the activity of enzymes such that one or more of the steps, e.g., one, two, three, four, five, six, seven, eight, nine, ten, or more of such steps, can be performed within a recombinant host. This disclosure provides host cells of any of the genera and species listed, and are genetically engineered to express one or more (e.g., two, three, four, five, six, seven, eight, nine, ten, 11, 12, or more) recombinant forms of any of the polypeptides having the activity of the enzymes recited in the disclosure. Thus, for example, the host cells can contain exogenous nucleic acids encoding polypeptides having the activity of enzymes catalyzing one or more of the steps of any of the pathways described herein.

In addition, this disclosure recognizes that where enzymes have been described as accepting CoA-activated substrates, analogous enzyme activities associated with [ACP]-bound substrates exist that are not necessarily in the same enzyme class.

Also, this disclosure recognizes that where enzymes have been described accepting (R)-enantiomers of substrates, analogous enzyme activities associated with (S)-enantiomer substrates exist that are not necessarily in the same enzyme class. This disclosure also recognizes that where an enzyme is shown to accept a particular co-factor, such as NADPH (dihydronicotinamide-adenine dinucleotide phosphate), or co-substrate, such as acetyl-CoA, many enzymes are promiscuous in terms of accepting a number of different co-factors or co-substrates in catalyzing a particular enzyme activity.

Also, this disclosure recognizes that where enzymes have high specificity for, e.g., a particular co-factor such as NADH (dihydronicotinamide adenine dinucleotide), an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the polypeptides having the activity of the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome-scale attenuation or knockout strategies for directing carbon flux to a C7 building block, for example, to achieve reduced flux to unwanted side products such as 7-hydroxyheptanoic acid and 1,7-heptanediol while achieving increased production of 7-AHA, pimelic acid, and heptamethylenediamine. Similarly, analysis can be utilized to devise genome-scale attenuation or knockout strategies for directing carbon flux to a C6 building block, for example, to achieve reduced flux to unwanted side products such as 6-hydroxyhaxanoic acid and 1,6-hexanediol while achieving increased production of 6-AHA, adipic acid, and hexamethylenediamine.

In some embodiments, attenuation strategies include but are not limited to the use of transposons, homologous recombination (double cross-over approach), PCR, including the one-step inactivation method based on PCR products developed by Datsenko and Wanner (2000), mutagenesis, enzyme inhibitors, antisense oligonucleotides, RNAi interference, and genome-editing technologies, including the CRISPR-Cas9 system or its equivalents.

In some embodiments, fluxomic, metabolomic, and transcriptomal data can be utilized to inform or support genome-scale system biology techniques, thereby devising genome-scale attenuation or knockout strategies in directing carbon flux to a C7 or C6 building block.

In some embodiments, the host microorganism's tolerance to high concentrations of a C7 or C6 building block can be improved through continuous cultivation in a selective environment.

In some embodiments, the host microorganism's endogenous biochemical network can be attenuated or augmented to (1) ensure the intracellular availability of 2-oxoadipate; (2) create an NADH or NADPH imbalance that may only be balanced via the formation of one or more C7 or C6 building blocks; (3) prevent degradation of central metabolites, central precursors leading to and including one or more C7 or C6 building blocks; and/or (4) ensure efficient efflux from the cell.

In some embodiments requiring the intracellular availability of acetyl-CoA and NADH for C7 or C6 building block synthesis, an endogenous gene encoding polypeptides having the activity of an enzyme that catalyzes the degradation of acetyl-CoA to ethanol such as the alcohol dehydrogenase encoded by adhE can be attenuated (Shen et al. (2011), supra).

In some embodiments, an endogenous gene encoding polypeptides having the activity of an aldehyde dehydrogenase is attenuated.

In some embodiments, endogenous genes encoding polypeptides having alcohol dehydrogenase and aldehyde dehydrogenase activities are attenuated.

In some embodiments, the efflux of a C7 or C6 building block across the cell membrane to the extracellular media can be enhanced or amplified by genetically engineering structural modifications to the cell membrane or increasing any associated transporter activity for a C7 or C6 building block.

In some embodiments, polypeptides having the activity of a specific adipate CoA-ligase classified, for example, in EC 6.2.A A can be overexpressed in the host organism to support degradation of the by-product formation of C6 aliphatics via adipate.

In some embodiments, polypeptides having the activity of a specific 7-hydroxyheptanoate 6-oxohexanoate dehydrogenase can be overexpressed in the host organism to support degradation of the by-product formation of C6 aliphatics via adipate.

In some embodiments, polypeptides having the activity of a propanoate CoA-ligase can be overexpressed in the host organism to support the re-use of the by-product formation of C3 aliphatics via propanoyl-CoA.

The efflux of heptamethylenediamine can be enhanced or amplified by overexpressing broad substrate-range, multidrug transporters such as Bit from *Bacillus subtilis* (Woolridge et al., J. Biol. Chem., 272(14):8864-8866 (1997)), AcrB and AcrD from *Escherichia coli* (Elkins & Nikaido, J. Bacteriol., 184(23), 6490-6499 (2002)), NorA from *Staphylococcus aereus* (Ng et al., Antimicrob. Agents Chemother., 38(6), 1345-1355 (1994)), or Bmr from *Bacillus subtilis* (Neyfakh, Antimicrob. Agents Chemother., 36(2), 484-485 (1992)).

The efflux of 7-aminoheptanoate and heptamethylenediamine can be enhanced or amplified by overexpressing a solute transporter such as the lysE transporter from *Corynebacterium glutamicum* (Bellmann et al., Microbiology, 147, 1765-1774 (2001)).

The efflux of pimelic acid can be enhanced or amplified by overexpressing a dicarboxylate transporter such as the SucE transporter from *Corynebacterium glutamicum* (Huhn et al., Appl. Microbiol. & Biotech., 89(2), 327-335).

Producing Carbon Based Building Blocks Using a Recombinant Host

Typically, one or more carbon based building blocks, in particular C4 through C15 buildings blocks, more particularly C7 or C6 building blocks can be produced by providing a host microorganism and culturing the provided microorganism with a culture medium containing a suitable carbon source as described above. In general, the culture media and/or culture conditions can be such that the microorganisms grow to an adequate density and produce a carbon based building block efficiently. For large-scale production processes, any method can be used such as those described elsewhere (*Manual of Industrial Microbiology and Biotechnology* (A. L. Demain and J. E. Davies eds., 2d ed. ASM Press); and *Principles of Fermentation Technology* (P. F. Stanbury and A. Whitaker, Pergamon)). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a carbon based building block. Once produced, any method can be used to isolate the carbon based building blocks. For example, C7 or C6 building blocks can be recovered selectively from the fermentation broth via adsorption processes. In the case of pimelic acid and 6-aminoheptanoic acid or adipic acid, the resulting eluate can be further concentrated via evaporation, crystallized via evaporative and/or cooling crystallization, and the crystals recovered via centrifugation. In the case of heptamethylenediamine and 1,7-heptanediol or hexamethylenediamine to 1,6-hexanediol, distillation may be employed to achieve the desired product purity.

The disclosure will be further described in the following examples, which do not limit the scope of the disclosure described in the claims.

EXAMPLES

Example 1

Enzyme Activity of Polypeptides Having the Activity of Carboxylate Reductase Using Pimelate as Substrate and Forming Pimelate Semialdehyde A nucleotide sequence encoding a HIS-tag was added to the nucleic acid sequences from *Segniliparus rugosus* and *Segniliparus rotundus* that encode polypeptides having the activity of the carboxylate reductases of SEQ ID NOs: 3 (EFV11917.1) and 5 (ADG98140.1), respectively, such that N-terminal HIS-tagged polypeptides having the activity of carboxylate reductases could be produced. Each of the modified genes was cloned into a pET Duet expression vector along with an sfp gene encoding HIS-tagged polypeptides having the activity of phosphopantetheine transferase from *Bacillus subtilis*, both under the T7 promoter. Each expression vector was transformed into a BL21 [DE3] *E. coli* host, and the resulting recombinant

*E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. Polypeptides having the activity of the carboxylate reductases and phosphopantetheine transferases were purified from the supernatant using Ni-affinity chromatography, diluted 10-fold into 50 mM HEPES buffer (pH=7.5), and concentrated via ultrafiltration.

Figure 6:
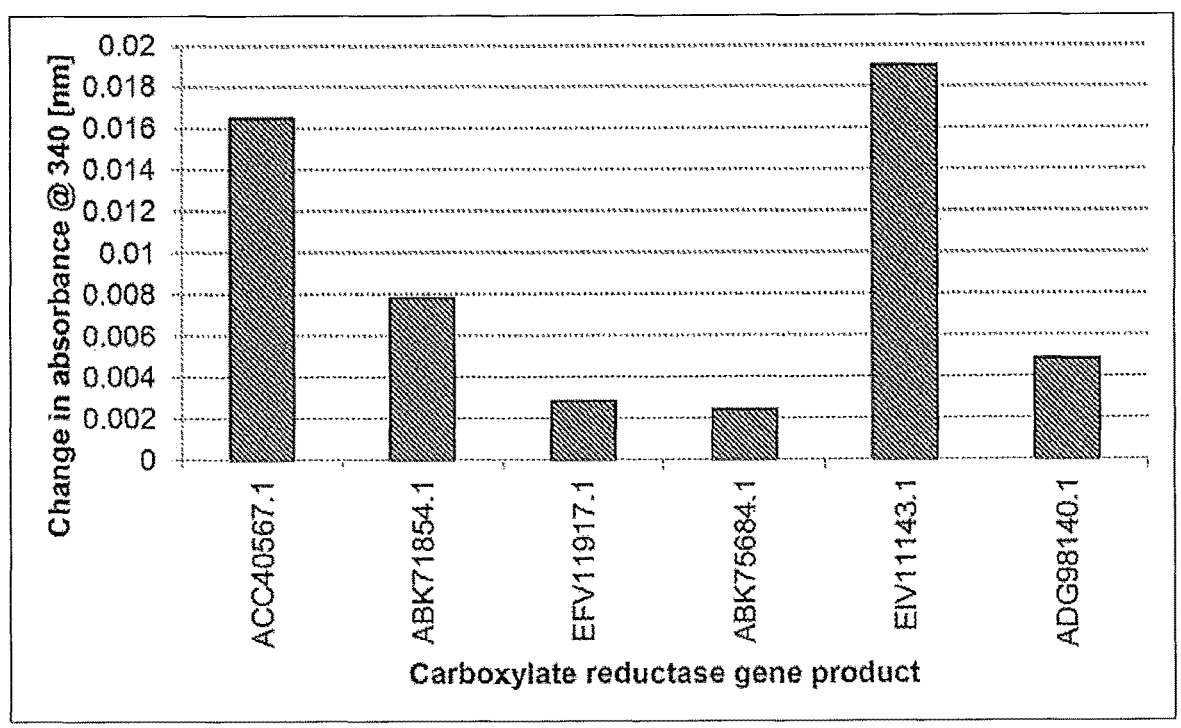
FIG. 6 is a bar graph summarizing the change in absorbance at 340 nm after 20 minutes, which is a measure of the consumption of NADPH and activity of six carboxylate reductase preparations in enzyme-only controls (no substrate).

Enzyme activity assays (i.e., from pimelate to pimelate semialdehyde) were performed in triplicate in a buffer composed of a final concentration of 50 mM HEPES buffer (pH=7.5), 2 mM pimelate, 10 mM MgCh, 1 mM ATP, and 1 mM NADPH. Each enzyme activity assay reaction was initiated by adding purified polypeptides having the activity of carboxylate reductase and phosphopantetheine transferase gene products or the empty vector control to the assay buffer containing the pimelate and then incubated at room temperature for 20 min. The consumption of NADPH was monitored by absorbance at 340 nm. Each enzyme-only control without pimelate demonstrated low base-line consumption of NADPH. See bars for EFV11917.1 and ADG98140.1 in FIG. 6.

Figure 7:
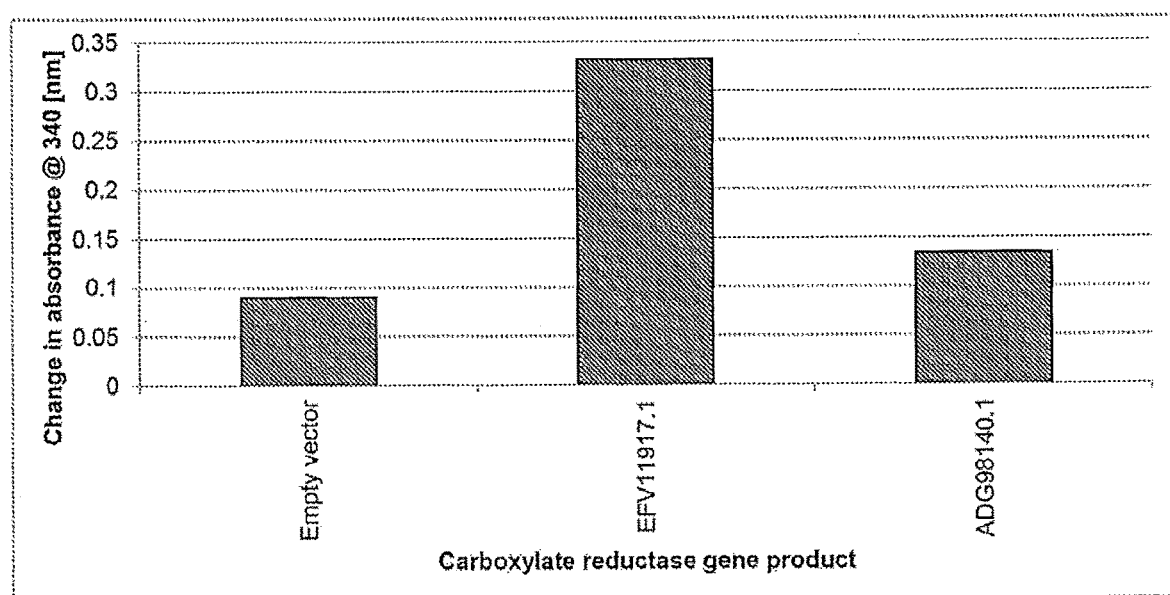
FIG. 7 is a bar graph of the change in absorbance at 340 nm after 20 minutes, which is a measure of the consumption of NADPH and the activity of two carboxylate reductase preparations for converting pimelate to pimelate semialdehyde relative to the empty vector control.

The gene products of SEQ ID NO: 3 (EFV11917.1) and SEQ ID NO: 5 (ADG98140.1), enhanced by the gene product of sfp, accepted pimelate as substrate, as confirmed against the empty vector control (see FIG. 7), and synthesized pimelate semialdehyde.

Example 2

Enzyme Activity of Polypeptides Having the Activity of ω-Transaminase Using Pimelate Semialdehyde as Substrate and Forming 7-Aminoheptanoate (7-AHA)

A nucleotide sequence encoding an N-terminal His-tag was added to the nucleic acid sequences from *Chromobacterium violaceum*, *Pseudomonas syringae*, *Rhodobacter sphaeroides*, and *Vibrio fluvialis* encoding polypeptides having the activity of the ω-transaminases of SEQ ID NOs: 7, 9, 10, and 12, respectively, such that N-terminal HIS-tagged polypeptides having the activity of ω-transaminases could be produced. Each of the resulting modified genes was cloned into a pET21a expression vector under control of the T7 promoter, and each expression vector was transformed into a BL21 [DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation, and the cell-free extract was used immediately in enzyme activity assays.

Enzyme activity assays in the reverse direction (i.e., 7-aminoheptanoate to pimelate semialdehyde) were performed in a buffer composed of a final concentration of 50 mM HEPES buffer (pH=7.5), 10 mM 7-aminoheptanoate, 10 mM pyruvate, and 100 μM pyridoxyl 5' phosphate. Each enzyme activity assay reaction was initiated by adding cell-free extract of the ω-transaminase gene product or the empty vector control to the assay buffer containing the 7-aminoheptanoate and incubated at 25° C. for 4 h, with shaking at 250 rpm. The formation of L-alanine from pyruvate was quantified via RP-HPLC.

Figure 9:
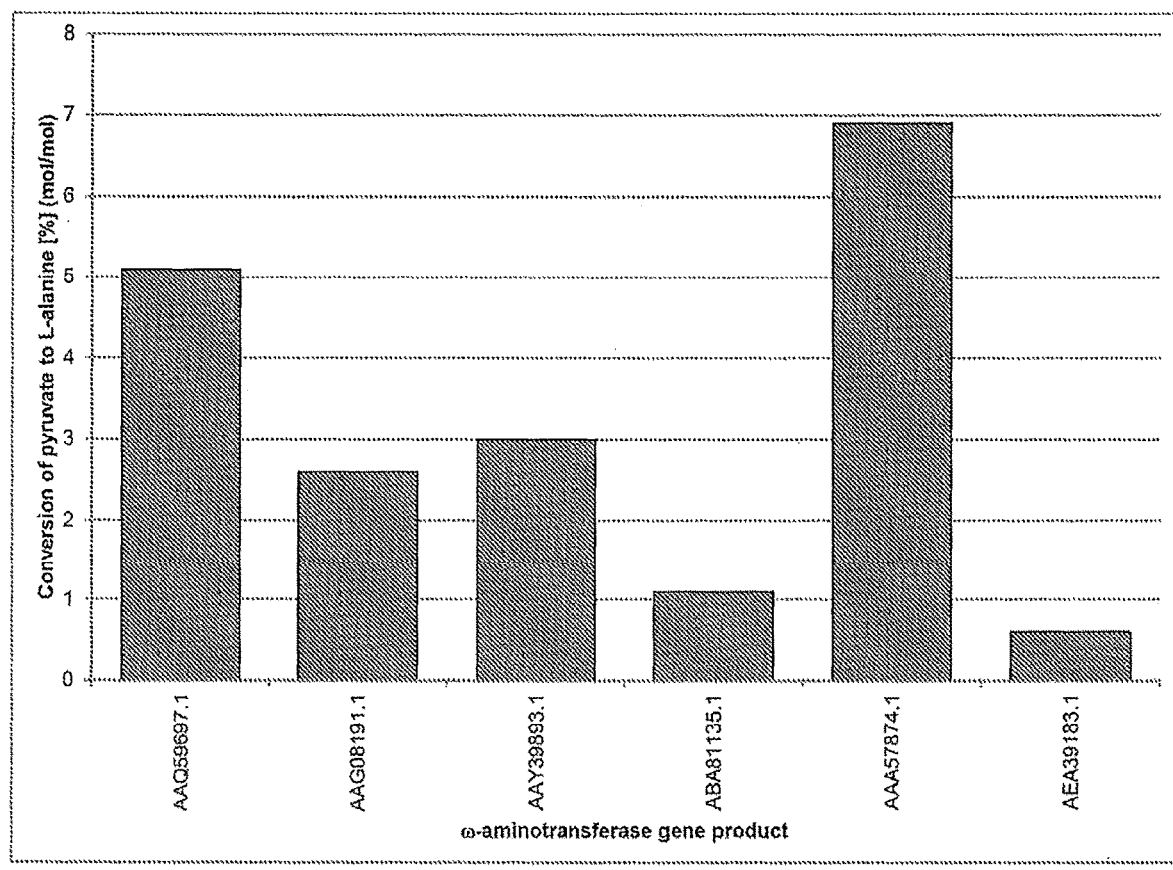
FIG. 9 is a bar graph summarizing the percent conversion of pyruvate to L-alanine (mol/mol) as a measure of the ω-transaminase activity of the enzyme-only controls (no substrate).
Figure 10:
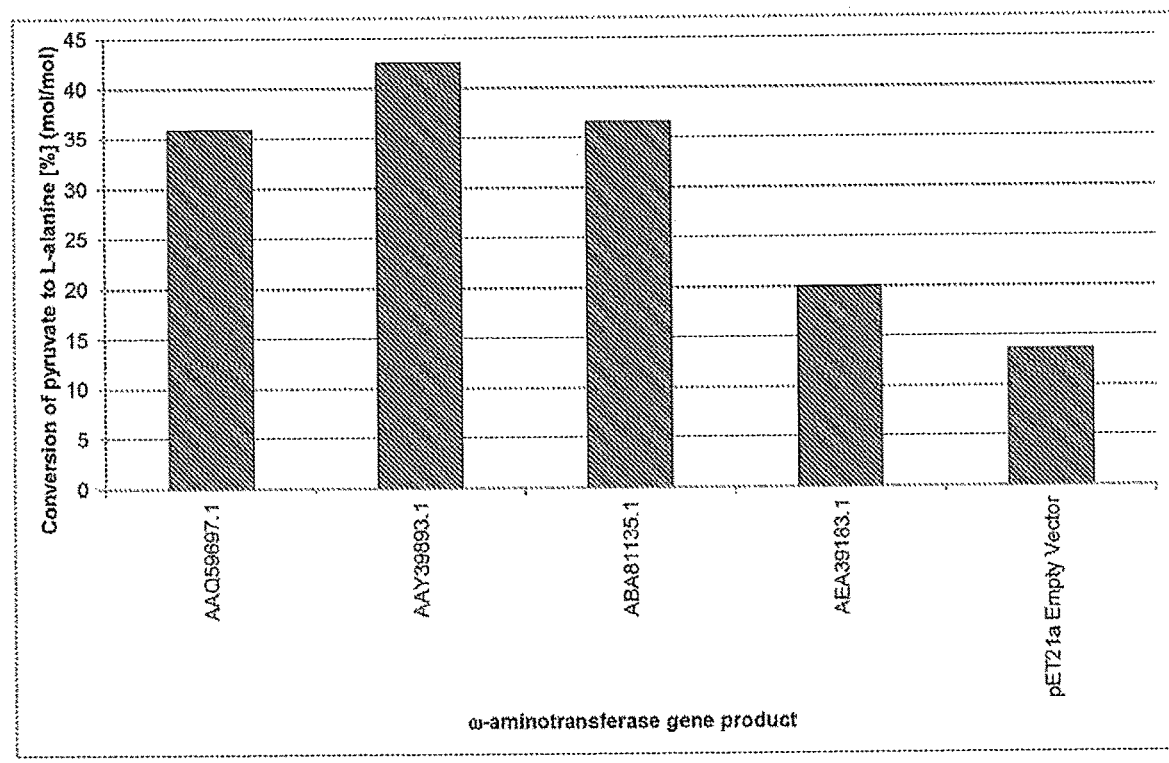
FIG. 10 is a bar graph of the percent conversion after 4 hours of pyruvate to L-alanine (mol/mol) as a measure of the ω-transaminase activity of four ω-transaminase preparations for converting 7-aminoheptanoate to pimelate semialdehyde relative to the empty vector control.

Each enzyme-only control without 7-aminoheptanoate demonstrated low base-line conversion of pyruvate to L-alanine. See FIG. 9. The gene product of SEQ ID NO: 7, SEQ ID NO: 9, SEQ ID NO: 10, and SEQ ID NO: 12 accepted 7-aminoheptanoate as substrate, as confirmed against the empty vector control. See FIG. 10.

Enzyme activity in the forward direction (i.e., pimelate semialdehyde to 7-aminoheptanoate) was confirmed for the polypeptides having the activity of transaminases of SEQ ID NO: 9, SEQ ID NO: 10, and SEQ ID NO: 12. Enzyme activity assays were performed in a buffer composed of a final concentration of 50 mM HEPES buffer (pH=7.5), 10 mM pimelate semialdehyde, 10 mM L-alanine, and 100 μM pyridoxyl 5' phosphate. Each enzyme activity assay reaction was initiated by adding a cell-free extract of the polypeptides having the activity of ω-transaminase gene product or the empty vector control to the assay buffer containing the pimelate semialdehyde and incubated at 25° C. for 4 h, with shaking at 250 rpm. The formation of pyruvate was quantified via RP-HPLC.

Figure 11:
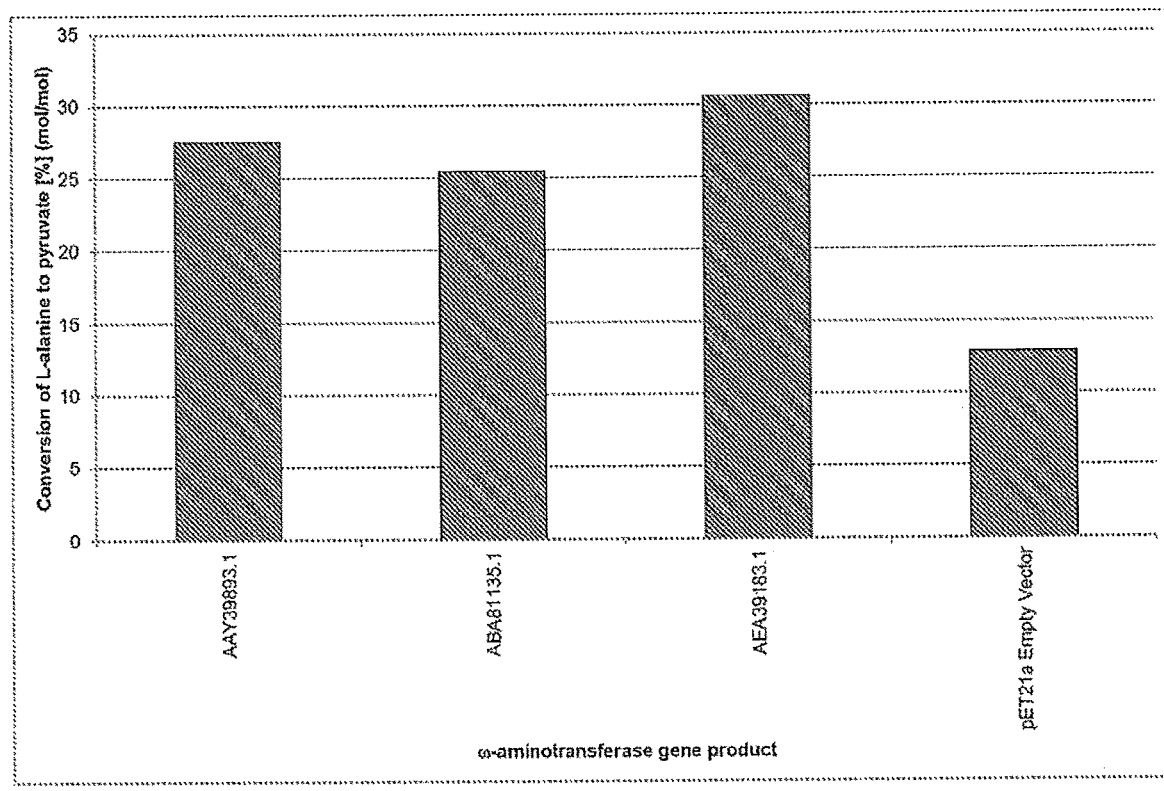
FIG. 11 is a bar graph of the percent conversion after 4 hours of L-alanine to pyruvate (mol/mol) as a measure of the ω-transaminase activity of three ω-transaminase preparations for converting pimelate semialdehyde to 7-aminoheptanoate relative to the empty vector control.

The gene product of SEQ ID NO: 9, SEQ ID NO: 10, and SEQ ID NO: 12 accepted pimelate semialdehyde as substrate, as confirmed against the empty vector control. See FIG. 11. The reversibility of the ω-transaminase activity was confirmed, demonstrating that the ω-transaminases of SEQ ID NO: 7, SEQ ID NO: 9, SEQ ID NO: 10, and SEQ ID NO: 12 accepted pimelate semialdehyde as substrate and synthesized 7-aminoheptanoate as a reaction product.

Example 3

Enzyme Activity of Polypeptides Having the Activity of Carboxylate Reductase Using 7-Hydroxyheptanoate as Substrate and Forming 7-Hydroxyheptanal A nucleotide sequence encoding a His-tag was added to the nucleic acids from *Mycobacterium marinum*, *Mycobacterium smegmatis*, *Segniliparus rugosus*, *Mycobacterium smegmatis*, *Mycobacterium massiliense*, and *Segniliparus rotundus* that encode polypeptides having the activity of the carboxylate reductases of SEQ ID NOs: 1-6, respectively (GenBank Accession Nos. ACC40567.1, ABK71854.1, EFV11917.1, EIV11143.1, ADG98140.1, and ABK75684.1, respectively), such that N-terminal HIS-tagged polypeptides having the activity of carboxylate reductases could be produced. Each of the modified genes was cloned into a pET Duet expression vector alongside an sfp gene encoding His-tagged polypeptides having the activity of phosphopantetheine transferase from *Bacillus subtilis*, both under control of the T7 promoter. Each expression vector was transformed into a BL21 [DE3] *E. coli* host along with the expression vectors from Example 3. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. Polypeptides having the activity of the carboxylate reductases and phosphopantetheine transferase were purified from the supernatant using Ni-affinity chromatography, diluted 10-fold into 50 mM HEPES buffer (pH=7.5), and concentrated via ultrafiltration.

Enzyme activity (i.e., 7-hydroxyheptanoate to 7-hydroxyheptanal) assays were performed in triplicate in a buffer composed of a final concentration of 50 mM HEPES buffer (pH=7.5), 2 mM 7-hydroxyheptanal, 10 mM MgCh, 1 mM ATP, and 1 mM NADPH. Each enzyme activity assay reaction was initiated by adding purified polypeptides having the activity of carboxylate reductase and phosphopantetheine transferase or the empty vector control to the assay buffer containing the 7-hydroxyheptanoate and then incubated at room temperature for 20 min. The consumption of NADPH was monitored by absorbance at 340 nm. Each enzyme-only control without 7-hydroxyheptanoate demonstrated low base-line consumption of NADPH. See FIG. 6.

Figure 8:
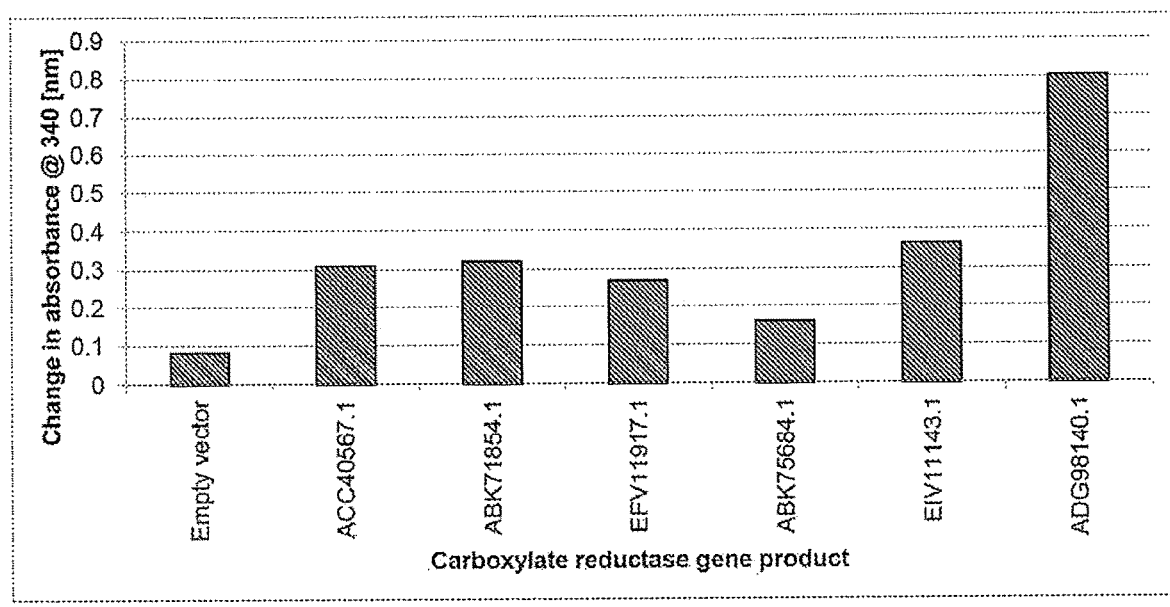
FIG. 8 is a bar graph of the change in absorbance at 340 nm after 20 minutes, which is a measure of the consumption of NADPH and the activity of six carboxylate reductase preparations for converting 7-hydroxyheptanoate to 7-hydroxyheptanal relative to the empty vector control.

The gene products of SEQ ID NOs: 1-6, enhanced by the gene product of sfp, accepted 7-hydroxyheptanoate as substrate, as confirmed against the empty vector control (see FIG. 8), and synthesized 7-hydroxyheptanal.

Example 4

Identification and Attenuation of Candidate ALR Genes in *E. coli* Strains to Direct Carbon Flux of the 7-AHA Biosynthesis Pathway In an effort to achieve improved alkane and aldehyde production from *E. coli*, prior work significantly increased isobutyraldehyde production in *E. coli* by deleting native isobutyraldehyde reductase (IBR) activities (Rodriguez and Atsumi (2012); Rodriguez and Atsumi (2014)). In the specific culture condition used therein, a total of about 44 candidate aldehyde reductase genes in *E. coli* genome were identified. The enhanced isobutyraldehyde producing strain, however, required simultaneous knockouts of 13 genes each encoding aldehyde reductase (ALR): AdhE, YqhD, AdhP, EutG, YiaY, YjgB, BetA, FucO, YahK, DkgA, YbbO, YghA, and GldA. Authors of the study also noted that additional ALR activity could still exist that may not have been expressed by the genome under the conditions used in the particular study, and that targeting certain ALRs for their specific endogenous expression, activity, and substrate profile could reduce the necessary gene deletion from 13 to 3-5 genes Significant reduction in the timeline and effort was achieved by careful selection of appropriate genes for deletion based on a combination of bioinformatic and biochemical approaches to identify ALR genes active in the desired growth conditions or induced by their cognate substrates.

Bioinformatic and gene expression data was used to identify ALR genes that are transcriptionally active under the desired growth conditions and also to identify ALR genes that are specifically induced in the presence of the aldehyde substrate. mRNA was extracted from *E. coli* strains grown in the presence or absence of the cognate aldehyde substrates, including but not limited to pimelic acid semialdehyde, adipic acid semialdehyde, pimelic acid semialdehyde methyl ester, and adipic acid semialdehyde methyl ester. Standard transcriptomic analysis was used to identify genes that are transcriptionally active, while differential analysis of strains grown in the presence or absence of an inducer was used to identify genes upregulated by the presence of the aldehyde substrates (Trapnell et al. (2012)). The same bioinformatic analysis was also conducted with the 7-AHA biosynthesis pathway for conversion of pimelic acid to 7-AHA by expressing the CAR gene and ω-TAM gene in *E. coli* strains. The ALR genes that were identified to be induced by the substrates or more highly expressed in the culture condition led to the selection of candidate genes for gene attenuation analysis. These analyses were repeated multiple times with ALR mutant strains to identify different ALR genes that may be induced due to the compensation effect where one or more genes took over the function of a deleted gene.

Metabolic functional assays of candidate ALR genes were further conducted to confirm the above bioinformatic findings and identify ALR genes that are capable of directing carbon flux in the 7-AHA biosynthesis pathway to increase production of pimelic acid, 7-AHA, or heptamethylenediamine while reducing production of 7-hydroxyheptanoate or 1,7-heptanediol. Single ALR mutants were screened in vivo by adding specific aldehyde compounds to growing cells and analyzing for the conversion of the aldehyde to the cognate alcohol. Aldehyde substrates used for this analysis included pimelic acid semialdehyde, adipic acid semialdehyde, pimelic acid semialdehyde methyl ester, and adipic acid semialdehyde methyl ester. Mutant strains showing reduced aldehyde reductase activities were selected and combined to generate strains with multiple mutations in ALR genes.

Alternatively, single ALR mutants were screened in vitro by adding specific aldehyde compounds to cell lysates/extracts and analyzing for the conversion of the aldehyde to the cognate alcohol and/or for the consumption of NAD(P)H cofactor. Aldehyde substrates used for this analysis included pimelic acid semialdehyde, adipic acid semialdehyde, pimelic acid semialdehyde methyl ester, and adipic acid semialdehyde methyl ester. Mutant strains showing reduced aldehyde reductase activities were selected and combined to generate strains with multiple mutations in ALR genes.

Further, single ALR mutants were also screened in the presence of the 7-AHA biosynthesis pathway for the conversion of pimelic acid to 7-AHA. *E. coli* strains with single ALR mutations were transformed with plasmids bearing the CAR gene (e.g., *S. rotundas*) and co-TAM gene (e.g., *C. violaceum*) for conversion of pimelic acid to 7-AHA via a pimelic acid semialdehyde intermediate. Mutant strains with reduced pimelic acid semialdehyde reductase activity produced less 7-hydroxypimelic acid as well as downstream products like 1,7-heptanediol and 7-aminoheptanol, while significantly increasing levels of 7-AHA when pimelic acid is being fed into the growth media. Mutant strains showing reduced aldehyde reductase activities were selected and combined to generate strains with multiple mutations in ALR genes.

Lastly, single and multiple mutant strains obtained from the above approaches were tested in comparison with wild-type strains to confirm systemic directing of carbon flux in the 7-AHA biosynthesis pathway exhibited by concurrent changes in the activity of key enzymes, including but not limited to carboxylate reductase using pimelate as substrate and forming pimelate semialdehyde (see Example 1), ω-transaminase using pimelate semialdehyde as substrate and forming 7-aminoheptanoate (see Example 2), and carboxylate reductase using 7-hydroxyheptanoate as substrate and forming 7-hydroxyheptanal (see Example 3).

Example 5

Assessment of by-Product Formation Via Aldehyde Dehydrogenase Activity in C7 and C6 Pathways The following Amp resistant strains were evaluated:

| Strain | Genotype | Genes |
|---|---|---|
| INV0728 | MG1655 rph +ΔbioF | Car_Srug, wta-Cv, lysE, sfp-Bs |
| INV0731 | MG1655 rph ++ΔbioF Δ12ADH | Car_Srug, wta-Cv, lysE, sfp-Bs |

Assay conditions were as follows:

| | |
|---|---|
| Strains | 2 |
| Medium | LP + 2 g/L alanine + amp |
| Volume | 2 mL (24 well plate) |
| Pre-culture | 6 mL + 6 µL gly stock |
| Growth & Feed | Back dilution to OD600 0.05 Feed 50 µL Pimelate/Adipate/7-AHA/6-AHA/No feed 6.24 mM final conc. |
| Temperature | 37° C., 280 rpm |
| Replicates | 3 |
| Analysis | OD600, LC-MS (pimelate, adipate, 7 AHA, 6-AHA, GC-MS non-derivatized (1,7-ehptanediol, 1,6-hexandiol), derivatized (pimelate, 7-AHA, 1,7-heptanediol, 7-aminoheptanol, 7-hydroxyheptanoate, 1,7-heptanediamine & equivalent C6) |
| Time Points | 24 hours |

Results are depicted in FIG. 13. As shown therein, strain INV0731 with 12 aldehyde dehydrogenase knockouts exhibited decreased unwanted by product production of 7-hydroxyheptanoic acid and 6-hydrohexanoic acid and increased production of desired products of 7-AHA and pimelic acid and 6-AHA and adipic acid in C7 and C6 building blocks, respectively.

REFERENCES

J. Beld, D. J. Lee, and M. D. Burkart, *Fatty acid biosynthesis revisited: structure elucidation and metabolic engineering*, Mol. Bio Syst., 11, 38 (2015).

J. A. Latham, D. Chen, K. N. Allen, and D. Dunaway-Mariano, *Divergence of Substrate Specificity and Function in the Escherichia coli Hotdog-fold Thioesterase Paralogs Ydil and YbdB*, Biochemistry, 53, 4775-4787 (2014).

S. Lin and J. E. Cronan, *The BioC O-methyltransferase catalyzes methyl esterification of malonyl-acyl carrier protein, an essential step in biotin synthesis*, Proc. Natl. Acad. Sci. USA, 109:17406-11 (2012).

M. D. McMahon and K. L. Prathera, *Functional Screening and In Vitro Analysis Reveal Thioesterases with Enhanced Substrate Specificity Profiles That Improve Short-Chain Fatty Acid Production in Escherichia coli*, Appl. and Environ. Microbiol., 80:1042-1050 (2014).

G. M. Rodriguez and S. Atsuma, *Isobutyraldehyde production from Escherichia coli by removing aldehyde reductase activity*, Microbial Cell Factories, 11:90 (2012).

G. M. Rodriguez and S. Atsuma, *Toward aldehyde and alkane production by removing aldehyde reductase activity in Escherichia coli*, Metabolic Engineering, 25:227-237 (2014).

W. R. Streit and P. Entcheva, *Biotin in microbes, the genes involved in its biosynthesis, its biochemical role and perspectives for biotechnological production*, Appl. Microbiol. Biotechnol. 61:21-31 (2003).

The invention claimed is:

1. A method for increasing biosynthesis of 7-aminoheptanoic acid or 6-aminohexanoic acid comprising:
   a) generating a recombinant *Escherichia coli* host by deleting three or more genes selected from the group consisting of adhE, yqhD, adhP, eutG, yjgB, yiaY, fucO, betA, eutE, yahK, yqhE, gldA, ybbO, and yghA, wherein said gene deletions reduce aldehyde reductase or alcohol dehydrogenase activity in said recombinant host;
   b) culturing said recombinant host in the presence of a substrate selected from pimelic acid semialdehyde, pimelic acid semialdehyde methyl ester, adipic acid semialdehyde, or adipic acid semialdehyde methyl ester and under conditions suitable for the conversion of said substrate to 7-aminoheptanoic acid or to 6-aminohexanoic acid via carboxylic acid reductase and ω-transaminase (ω-TAM); and
   c) obtaining increased production of the 7-aminoheptanoic acid or 6-aminohexanoic acid as compared to an *Escherichia coli* host without the three or more gene deletions.

2. The method of claim 1, wherein the recombinant *Escherichia coli* host is:
   cultured under aerobic, anaerobic, micro-aerobic or mixed oxygen/denitrification cultivation conditions;
   cultured under conditions of nutrient limitation;
   retained using a ceramic hollow fiber membrane to maintain a high cell density during fermentation; and/or fed a principal carbon source obtained from biological or non-biological feedstocks.

3. The method of claim 2, wherein the biological feedstock is monosaccharides, disaccharides, lignocellulose, hemicellulose, cellulose, lignin, levulinic acid, formic acid, triglycerides, glycerol, fatty acids, agricultural waste, condensed distillers' solubles, or municipal waste or the non-biological feedstock is or obtained from natural gas, syngas, CO2/H2, CO2, methanol, ethanol, benzoate, non-volatile residue (NVR) caustic wash waste stream from cyclohexane oxidation processes, or terephthalic acid/isophthalic acid mixture waste streams.

4. The method of claim 1, wherein tolerance of the recombinant *Escherichia coli* host to high concentrations of a C7 or C6 building block is improved through continuous cultivation in a selective environment.

5. The method of claim 1, wherein the recombinant *Escherichia coli* host comprises:
(i) an alteration of activity of one or more of the following: polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the NADH or NADPH imbalance, a glutamate dehydrogenase dissipating the NADH or NADPH imbalance, a NADH/NADPH-utilizing glutamate dehydrogenase, a pimeloyl-CoA dehydrogenase; an acyl-CoA dehydrogenase accepting C7 building blocks and central precursors as substrates; a glutaryl-CoA dehydrogenase; or a pimeloyl-CoA synthetase; and/or
(ii) an alteration to overexpress one or more of the following: an acetyl-CoA synthetase, a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; L-alanine dehydrogenase; a L-glutamate dehydrogenase specific to the NADH or NADPH used to generate a co-factor imbalance; a methanol dehydrogenase, a formaldehyde dehydrogenase, a diamine transporter; a dicarboxylate transporter; an S-adenosylmethionine synthetase and/or a multidrug transporter.

* * * * *